United States Patent
Stauffer et al.

(10) Patent No.: US 8,293,759 B2
(45) Date of Patent: Oct. 23, 2012

(54) SPIROPIPERIDINE BETA-SECRETASE INHIBITORS FOR THE TREATMENT OF ALZHEIMER'S DISEASE

(75) Inventors: Shaun R. Stauffer, Schwenksville, PA (US); Ivory D. Hills, Harleysville, PA (US); Ashley Nomland, Sellersville, PA (US)

(73) Assignee: Merck, Sharp & Dohme, Corp., Rahway, NJ (US)

( * ) Notice: Subject to any disclaimer, the term of this patent is extended or adjusted under 35 U.S.C. 154(b) by 597 days.

(21) Appl. No.: 12/447,802

(22) PCT Filed: Oct. 29, 2007

(86) PCT No.: PCT/US2007/022819
§ 371 (c)(1),
(2), (4) Date: Apr. 29, 2009

(87) PCT Pub. No.: WO2008/054698
PCT Pub. Date: May 8, 2008

(65) Prior Publication Data
US 2010/0069419 A1 Mar. 18, 2010

Related U.S. Application Data

(60) Provisional application No. 60/855,180, filed on Oct. 30, 2006.

(51) Int. Cl.
*C07D 471/10* (2006.01)
*C07D 471/20* (2006.01)
*A61K 31/438* (2006.01)

(52) U.S. Cl. .......................... 514/278; 546/20
(58) Field of Classification Search ............... 546/20; 514/278
See application file for complete search history.

(56) References Cited

U.S. PATENT DOCUMENTS

| | | | |
|---|---|---|---|
| 5,534,520 | A | 7/1996 | Fisher et al. |
| 5,852,029 | A | 12/1998 | Fisher et al. |
| 2005/0256108 | A1 | 11/2005 | Schlienger |
| 2007/0021454 | A1 | 1/2007 | Coburn et al. |
| 2007/0197571 | A1 | 8/2007 | Barrow et al. |
| 2010/0029701 | A1 | 2/2010 | Nantermet et al. |
| 2010/0069419 | A1 | 3/2010 | Stauffer et al. |
| 2010/0298342 | A1 | 11/2010 | Egbertson et al. |

FOREIGN PATENT DOCUMENTS

| | | |
|---|---|---|
| WO | WO 99/65494 | 12/1999 |
| WO | WO 03/057698 | 7/2003 |
| WO | WO 2004/037800 | 5/2004 |
| WO | WO 2004/050039 | 6/2004 |
| WO | WO2006/044497 | 4/2006 |
| WO | WO 2006/044497 | 4/2006 |
| WO | WO2007/011810 | 1/2007 |
| WO | WO 2007/011833 | 1/2007 |
| WO | WO2007/011833 | 1/2007 |
| WO | WO 2007/087448 | 8/2007 |
| WO | WO 2008/030412 | 3/2008 |
| WO | WO2008/030412 | 3/2008 |
| WO | WO2008/045250 | 4/2008 |
| WO | WO2008/054698 | 5/2008 |

OTHER PUBLICATIONS

Science Daily, 2008, New Alzheimer's treatment completes first phase of testing.*
Dorwald F. A. Side Reactions in Organic Synthesis, 2005, Wiley: VCH Weinheim pg. IX of Preface. Also see pp. 8 and 9.*
Chem Registry No. 128221-95-4 (Jul. 13, 1990).
Chem Registry No. 150358-83-1 (Sep. 30, 1993).
Chem Registry No. 29096-07-9 (Nov. 16, 1984).

* cited by examiner

*Primary Examiner* — Rita Desai
(74) *Attorney, Agent, or Firm* — Keith D. MacMillan; Gerard M. Devlin

(57) ABSTRACT

The present invention is directed to spiropiperidine compounds of formula (I)

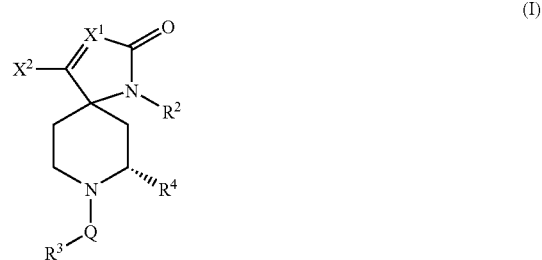

(I)

which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

10 Claims, No Drawings

SPIROPIPERIDINE BETA-SECRETASE INHIBITORS FOR THE TREATMENT OF ALZHEIMER'S DISEASE

CROSS-REFERENCE TO RELATED APPLICATIONS

This application claims priority under 35 U.S.C. §119(e) of U.S. provisional application Ser. No. 60/855,180, filed Oct. 30, 2006.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to spiropiperidine compounds which are useful as inhibitors of the beta secretase enzyme, and are useful in the treatment of diseases in which the beta secretase enzyme is involved, such as Alzheimer's Disease.

BACKGROUND OF THE INVENTION

Alzheimer's Disease is a progressive, neurodegenerative disorder characterized by memory impairment and cognitive dysfunction. Alzheimer's disease is characterized pathologically by the deposition of amyloid in the brain in the form of extra-cellular plaques and intra-cellular neurofibrillary tangles.

The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_S$). Proteases that release APP and its fragments from the membrane are termed "secretases." Most $APP_S$ is released by a putative α-secretase which cleaves within the Aβ protein to release α-$APP_S$ and precludes the release of intact Aβ. A minor portion of $APP_S$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the cleavage of APP, production of Aβ, and accumulation of β amyloid plaques in the brain, which is characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochem. Biophys. Res. Comm, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to compounds of general formula (I)

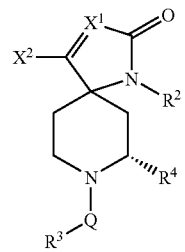

(I)

and pharmaceutically acceptable salts thereof, which are useful as inhibitors of the β-secretase enzyme.

The invention is also directed to pharmaceutical compositions which include a therapeutically effective amount of a compound of formula (I), or a pharmaceutically acceptable salt thereof, and a pharmaceutically acceptable carrier. The invention is also directed to methods of treating mammals for diseases in which the β-secretase enzyme is involved, such as Alzheimer's disease, and the use of the compounds and pharmaceutical compositions of the invention in the treatment of such diseases.

DETAILED DESCRIPTION OF THE INVENTION

In one embodiment, the present invention is directed to spiropiperidine compounds of general formula (I)

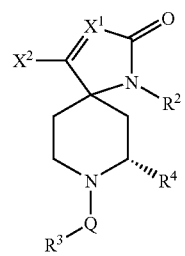

(I)

wherein:
$X^1$ is selected from the group consisting of
  (1) N, and
  (2) $CR^7$, wherein $R^7$ is selected from the group consisting of
    (a) hydrogen,
    (b) —$C_{1-10}$ alkyl, wherein said alkyl is optionally substituted with halogen,
    (c) halogen,
    (d) —OH, or
    (e) —$OC_{1-10}$ alkyl, wherein said alkyl is optionally substituted with halogen;
$X^2$ is selected from the group consisting of
  (1) —$NR^{1A}R^{1B}$, wherein $R^{1A}$ and $R^{1B}$ are each selected from the group consisting of
    (a) —$C_{1-10}$ alkyl, or
    (b) aryl, wherein said alkyl is optionally substituted with one or more
(i) halo,
(ii) —OH,
(iii) aryl, or
(iv) —CN,
and said aryl is optionally substituted with one or more
(i) halo,
(ii) —OH,
(iii) —CN,
(iv) —$C_{1-10}$ alkyl,
(v) —$C_{3-12}$ cycloalkyl,
(vi) —O—$C_{1-10}$ alkyl,
(vii) —$C_{0-6}$ alkyl-aryl,
or $R^{1A}$ and $R^{1B}$ are linked together with the nitrogen to which they are attached to form a ring structure comprising three to nine ring carbon atoms, wherein one or more of said ring carbon atoms is optionally substituted with one or more
(a) halo,
(b) —OH,
(c) —CN,
(d) —$C_{1-10}$ alkyl
(e) —$C_{3-12}$ cycloalkyl,
(f) —O—$C_{1-10}$ alkyl,
(g) —$C_{0-6}$ alkyl-aryl,
wherein said alkyl, cycloalkyl or aryl moiety is optionally substituted with one or more
(i) halo,
(ii) —OH,
(iii) —CN,
(iv) —$C_{1-6}$ alkyl,
(v) —$C_{2-6}$ alkenyl,
(vi) —$OC_{1-6}$ alkyl, or
(vii) —$C_{1-6}$ haloalkyl,
(2) —$C_{1-10}$ alkyl
(3) —$C_{3-12}$ cycloalkyl,
(4) —$C_{1-10}$ alkynyl,
(5) aryl, and
(6) heteroaryl,
wherein said $X^2$ alkyl, cycloalkyl, aryl or alkynyl moiety is optionally substituted with one or more
(a) —$C_{1-10}$ alkyl,
(b) halo,
(c) —OH,
(d) —CN,
(e) —O—$C_{1-10}$ alkyl, or
(f) —$C_{0-6}$ alkyl-aryl;
$R^2$ is selected from the group consisting of
(1) hydrogen,
(2) —$C_{1-10}$ alkyl,
(3) —$C_{2-10}$ alkenyl,
(4) —$C_{2-10}$ alkynyl,
(5) —$C_{3-12}$ cycloalkyl,
(6) a non-aromatic heterocyclic group having 4 to 8 ring atoms, wherein one ring atom is a heteroatom selected from the group consisting of nitrogen and oxygen,
(7) aryl, and
(8) heteroaryl,
wherein said alkyl, cycloalkyl, heterocyclic group, alkenyl, alkynyl, aryl or heteroaryl $R^2$ moiety is optionally substituted with one or more
(a) halo,
(b) —OH,
(c) —CN,
(d) —$C_{1-10}$ alkyl
(e) —$C_{3-12}$ cycloalkyl,
(f) —O—$C_{1-10}$ alkyl,
(g) —$C_{0-6}$ alkyl-aryl,
(h) —$C_{0-6}$ alkyl-heteroaryl,
(i) —NC(=O)—$NR^6R^{6\prime}$;
(j) —NC(=O)—$C_{1-3}$ alkyl-$NR^6R^{6\prime}$;
(k) —NC(=O)$R^6$
(l) —$NR^6R^{6\prime}$,
(m) —$SO_2R^6$,
(n) —$SO_2NR^6R^{6\prime}$, or
(o) a non-aromatic heterocyclic group having 4 to 8 ring atoms, wherein one ring atom is a heteroatom selected from the group consisting of nitrogen and oxygen, and said alkyl, cycloalkyl, aryl, heteroaryl and heterocyclic moiety is optionally substituted with one or more
(i) halo,
(ii) —OH,
(iii) —CN,
(iv) —$C_{1-10}$ alkyl, wherein said alkyl is optionally substituted with one or more halo,
(v) —$OC_{1-10}$ alkyl, wherein said alkyl is optionally substituted with one or more halo,
(vi) —$SO_2C_{1-3}$ alkyl,
(vii) —$SO_2NR^6R^{6\prime}$,
(viii) —$NR^6SO_2C_{1-3}$alkyl,
(ix) —$CO_2R^6$, and
(x) —$CONR^6R^{6\prime}$;
Q is a bond or —$C_{1-6}$ alkyl, wherein said alkyl is optionally substituted with one or more
(a) halo,
(b) —OH,
(c) —CN,
(d) —$C_{1-10}$ alkyl
(e) —$C_{3-12}$ cycloalkyl,
(f) —O—$C_{1-10}$ alkyl,
(g) aryl, and
(h) heteroaryl;
$R^3$ is selected from the group consisting of
(1) hydrogen,
(2) —$C_{1-10}$ alkyl,
(3) —$C_{2-10}$ alkenyl,
(4) —$C_{2-10}$ alkynyl,
(5) —$C_{3-12}$ cycloalkyl,
(6) —$C_{3-12}$ cycloalkenyl,
(7) aryl, and
(8) heteroaryl,
wherein said alkyl, cycloalkyl, cycloalkenyl, alkenyl, alkynyl, aryl or heteroaryl $R^3$ moiety is optionally substituted with one or more
(a) halo,
(b) —OH,
(c) —CN,
(d) —$C_{1-10}$ alkyl,
(e) —$C_{2-10}$ alkenyl,
(f) —$C_{3-12}$ cycloalkyl,
(g) —O—$C_{3-12}$ cycloalkyl,
(h) —O—$C_{1-10}$ alkyl,
(i) —O—$C_{3-12}$ heterocyclic, wherein said heterocyclic group has from 4 to 8 ring atoms, wherein one ring atom is a heteroatom selected from the group consisting of nitrogen, sulfur and oxygen,
(j) aryl,
(k) heteroaryl,
(l) —$NR^6R^{6\prime}$,
and said alkyl, alkenyl, cycloalkyl, aryl and heteroaryl moiety is optionally substituted with one or more
(i) halo,
(ii) —OH, (iii) —CN,
(iv) —$C_{1-10}$ alkyl,
(v) —$OC_{1-10}$ alkyl,
(vi) —$NR^6R^{6t}$,
(vii) —$C_{2-6}$ alkenyl,
(viii) —$C_{1-6}$ haloalkyl,
(ix) —$SO_2C_{1-3}$ alkyl,
(x) —$SO_2NR^6R^{6t}$, or
(xi) —$CONR^6R^{6t}$, provided that when Q is a bond then $R^3$ is hydrogen;
$R^4$ is selected from the group consisting of
(1) hydrogen,
(2) —$C_{1-10}$ alkyl,
(3) —$C_{3-4}$ alkenyl, and
(4) aryl,
wherein said alkyl, alkenyl or aryl $R^4$ group is optionally substituted with one or more
  (a) halo,
  (b) —OH
  (c) —$C_{1-6}$ alkyl,
  (d) —CN,
  (e) —O—$C_{1-10}$ alkyl,
  (f) —$NR^8R^9$, wherein $R^8$ and $R^9$ are selected from the group consisting of
    (i) hydrogen, and
    (ii) —$C_{1-6}$ alkyl,
  (g) —$S(O)_n$—$C_{1-6}$ alkyl, wherein n is 0, 1 or 2,
  (h) —C(=O)—$R^7$, wherein $R^7$ is selected from the group consisting of
    (i) hydrogen,
    (ii) OH,
    (iii) —$C_{1-6}$ alkyl, and
    (iv) —$OC_{1-6}$ alkyl, and
    (v) aryl;

$R^6$ and $R^{6t}$ are selected from the group consisting of
(1) hydrogen,
(2) —$C_{1-6}$ alkyl,
(3) —$C_{3-7}$ cycloalkyl,
(4) —$C_{1-6}$ haloalkyl,
(5) —$C_{0-6}$ alkyl-aryl,
(6) —$C_{0-6}$alkyl-heteroaryl,
(7) halo, and
(8) a non-aromatic heterocyclic group having 4 to 8 ring atoms, wherein one ring atom is a heteroatom selected from the group consisting of nitrogen and oxygen,
wherein said aryl or heteroaryl $R^6$ or $R^{6t}$ moiety is optionally substituted with one or more
  (a) halo,
  (b) —$C_{1-6}$ alkyl,
  (c) —O—$C_{1-6}$ alkyl, and
  (d) —$NO_2$; and
and pharmaceutically acceptable salts thereof.

In one embodiment of the compounds of formula (I), $X^1$ is N.

In one embodiment of the compounds of formula (I), $X^1$ is $NR^{1A}R^{1B}$, wherein $R^{1A}$ and $R^{1B}$ are linked together with the nitrogen to which they are attached to form a ring structure comprising three to nine ring carbon atoms, wherein one or more of said ring carbon atoms is optionally substituted with one or more
(a) halo,
(b) —$C_{1-10}$ alkyl
(c) —$C_{3-12}$ cycloalkyl,
(d) —O—$C_{1-10}$ alkyl,
(e) —$C_{0-6}$ alkyl-aryl, wherein said alkyl, cycloalkyl or aryl moiety is optionally substituted with one or more
  (i) halo,
  (ii) —$C_{1-6}$ alkyl,
  (iii) —$OC_{1-6}$ alkyl, or
  (iv) —$C_{1-6}$ haloalkyl.

In another embodiment, $X^2$ is $NR^{1A}R^{1B}$, wherein $R^{1A}$ and $R^{1B}$ are each optionally substituted $C_{1-10}$ alkyl (suitably $C_{1-6}$ alkyl). In an alternative embodiment, $R^{1A}$ is aryl and $R^{1B}$ is optionally substituted $C_{1-10}$ alkyl (suitably $C_{1-6}$ alkyl).

In one embodiment, $R^2$ is aryl (for example, phenyl), which is optionally substituted with one or more
(a) halo,
(b) —OH,
(c) —CN,
(d) —$C_{1-10}$ alkyl,
(e) —$C_{3-12}$ cycloalkyl,
(f) —O—$C_{1-10}$ alkyl, and
(g) —$C_{0-6}$ alkyl-aryl, wherein said aryl is optionally substituted with one or more
  (i) halo,
  (ii) —OH,
  (iii) —$SO_2R^6$, or
  (iv) —$SO_2NR^6R^{6t}$, and
(h) —$C_{0-6}$ alkyl-heteroaryl.

In one embodiment of the compounds of formula (I), Q is a —$C_{1-3}$ alkyl, for example —$CH_2$—, and $R^3$ is selected from the group consisting of
(1) —$C_{1-10}$ alkyl,
(2) —$C_{2-10}$ alkynyl,
(3) —$C_{3-12}$ cycloalkyl,
(4) aryl, and
(5) heteroaryl,
wherein said alkyl, cycloalkyl, alkynyl, aryl or heteroaryl $R^3$ moiety is optionally substituted with one or more
  (a) halo,
  (b) —OH,
  (c) —$C_{1-10}$ alkyl,
  (d) —$C_{3-12}$ cycloalkyl, or
  (e) —O—$C_{1-10}$ alkyl.

In one embodiment of the compounds of formula (I), $R^4$ is —$C_{1-10}$ alkyl (for example, methyl) or —$C_{3-4}$ alkenyl.

The invention is also directed to methods of treating mammals for diseases in which the β-secretase enzyme is involved, such as Alzheimer's disease, by administering a therapeutically effective amount of a compound of formula (I).

The invention is also directed to pharmaceutical compositions which include an effective amount of a compound of formula (I) or pharmaceutically acceptable salts thereof, and a pharmaceutically acceptable carrier.

The invention is further directed to a method for the manufacture of a medicament or a composition for inhibiting β-secretase enzyme activity in humans and animals comprising combining a compound of formula (I) or a pharmaceutically acceptable salt thereof, with a pharmaceutical carrier or diluent.

Within the genus of compounds of formula (I), there is a sub-genus of compounds of formula (II):

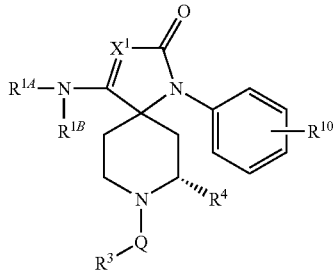

wherein $X^1$, $R^{1A}$, $R^{1B}$, Q, $R^3$ and $R^4$ are as described above, and $R^{10}$ is selected from the group consisting of
(a) halo,
(b) —OH,
(c) —CN,
(d) —$C_{1-10}$ alkyl
(e) —$C_{3-12}$ cycloalkyl,
(f) —O—$C_{1-10}$ alkyl,
(g) $C_{0-6}$ alkyl-aryl, wherein said aryl is optionally substituted with one or more
   (i) halo,
   (ii) —OH,
   (iii) —CN,
   (iv) —$C_{1-6}$ alkyl,
   (v) —$C_{2-6}$ alkenyl,
   (vi) —$OC_{1-6}$ alkyl,
   (vii) —$C_{1-6}$ haloalkyl,
   (viii) —$SO_2C_{1-3}$ alkyl,
   (ix) —$SO_2NR^6R^{6'}$, or
   (x) —$CONR^6R^{6'}$;
(h) —$C_{0-6}$ alkyl-heteroaryl,
(i) —NC(=O)—$NR^6R^{6'}$,
(j) —NC(=O)—$C_{1-3}$ alkyl-$NR^6R^{6'}$,
(k) —NC(=O)$R^6$,
(l) —$NR^6R^{6'}$, and
(m) a non-aromatic heterocyclic group having 4 to 8 ring atoms, wherein one ring atom is a heteroatom selected from the group consisting of nitrogen and oxygen, and said alkyl, cycloalkyl and heteroaryl $R^{10}$ moiety is optionally substituted with one or more
   (i) halo,
   (ii) —OH,
   (iii) —CN,
   (iv) —$C_{1-10}$ alkyl,
   (v) —$OC_{1-10}$ alkyl,
   (vi) —$SO_2C_{1-3}$ alkyl,
   (vii) —$SO_2NR^6R^{6'}$,
   (viii) —$NR^6SO_2C_{1-3}$alkyl,
   (ix) —$CO_2R^6$, and
   (x) —$CONR^6R^{6'}$,
and pharmaceutically acceptable salts.

In one embodiment, the invention is directed to methods of inhibiting BACE1 enzyme activity, by administering a therapeutically effective amount of a compound of formula (I).

In another embodiment, the invention is directed to methods of inhibiting BACE2 enzyme activity, by administering a therapeutically effective amount of a compound of formula (I).

The invention is also directed to a method for the manufacture of a medicament or a composition for treating Alzheimer's Disease in humans, comprising combining a compound of formula (I) or a pharmaceutically acceptable salt thereof, with a pharmaceutical carrier or diluent.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Suitable alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

The term "$C_0$ alkyl," for example in the term "—$C_0$alkyl-$C_{6-12}$ aryl", refers to a bond.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Suitable alkenyl groups for use in the invention are $C_{2-6}$ alkenyl groups, having from two to six carbon atoms. Exemplary alkenyl groups include ethenyl and propenyl.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Suitable alkynyl groups for use in the invention are $C_{2-6}$ alkynyl groups, having from two to six carbon atoms. Exemplary alkynyl groups include ethynyl and propynyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, as well as bridged and fused ring carbocycles, such as Spiro fused ring systems.

Suitable cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantly and norbornyl. Exemplary fused cycloalkyl groups include decahydronaphthalene.

As used herein, the term "heterocyclic," by itself or as part of another substituent, means a cycloalkyl group as defined above, in which one or more of the ring carbon atoms is replaced with a heteroatom (such as N or O). Suitable non-aromatic heterocyclic groups for use in the invention include piperidinyl, piperazinyl, morpholinyl, tetrahydropyranyl, tetrahydrofuranyl, pyrrolidinyl, pyrazolidinyl and imidazolildinyl. In one embodiment, heterocyclic groups for use in the invention have four to eight ring atoms and a single nitrogen or oxygen heteroatom.

When a heterocyclic group as defined herein is substituted, the substituent may be bonded to a ring carbon atom of the heterocyclic group, or to a ring heteroatom (i.e., a nitrogen, oxygen or sulfur), which has a valence which permits substitution. Suitably, the substituent is bonded to a ring carbon atom. Similarly, when a heterocyclic group is defined as a substituent herein, the point of attachment may be at a ring carbon atom of the heterocyclic group, or on a ring heteroatom (i.e., a nitrogen, oxygen or sulfur), which has a valence which permits attachment. In one embodiment, the attachment is at a ring carbon atom.

As used herein, the term "aryl," by itself or as part of another substituent, means an aromatic or cyclic radical having the number of carbon atoms designated (e.g., $C_{6-10}$ aryl means an aryl group having from six to ten carbons atoms). The term "aryl" includes multiple ring systems (such as fused ring systems) as well as single ring systems, and includes multiple ring systems wherein part of the molecule is aromatic and part is non-aromatic. A suitable single ring aryl group for use in the invention is phenyl. Suitable fused ring aryl groups include naphthyl, tetrahydronaphthyl and indanyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). The term "heteroaryl" includes multiple ring systems as well as single ring systems. Suitable heteroaryl groups have from 5 to 12 ring atoms. Exemplary heteroaryl groups include pyrazinyl, pyrazolyl, pyridazinyl, pyridyl, pyrimidinyl, pyrrolyl, tetrazolyl, furanyl, imidazolyl, indazolyl, triazinyl, pyranyl, thiazolyl, thienyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. In one embodiment, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. In one embodiment, the attachment is at a ring carbon atom.

As used herein, the term "beta-secretase" or "β-secretase" refers to an enzyme that is sometimes known in the literature as "BACE", "BACE1" (see, e.g., Vassar et al., 1999, *Science* 286:735-741), or "BACE2" (see, e.g., Farzan et al., 2000, *PNAS* 97:9712-9717). BACE1 is a 501 amino acid membrane-bound aspartic protease. BACE1 has all the known functional properties and characteristics of β-secretase. BACE2, also called Asp-1 or memapsin-1, is a second member of the BACE family of membrane-bound aspartic proteases. See Roggo, *Current Topics in Medicinal Chemistry*, 2002, 2:359-370, for a further discussion of the differences between BACE1 and BACE2.

The compounds of the invention are inhibitors of both the BACE1 and BACE2 enzyme.

The compounds of formula (I) have at least one asymmetric center. Additional asymmetric centers may be present depending upon the nature of the various substituents on the molecule.

Compounds with asymmetric centers give rise to enantiomers (optical isomers), diastereomers (configurational isomers) or both. All of the possible enantiomers and diastereomers in mixtures (as pure or partially purified compounds) are included within the scope of formula (I).

Compounds described herein may contain one or more double bonds, and may thus give rise to cis/trans isomers as well as other configurational isomers. The compounds of formula (I) include all such possible isomers as well as mixtures of such isomers.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The compounds of the invention may be prepared according to the following reaction Schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

The present invention also provides a method for the synthesis of compounds useful as intermediates in the preparation of compounds of the invention.

Scheme 1A outlines the synthesis of examples of type 1A.8 and 1A.9. Starting from 4-methoxypyridine (1A.1) piperidinone 1A.2 is prepared using an appropriate Grignard reagent in the presence of CbzCl followed by Zn/HOAc reduction to give desired piperidinone 1A.2. The Cbz protected piperidinone can take part in a Strecker reaction in the presence of $Zn(CN)_2$ to give the desired stereoisomeric Strecker product as the major isomer. Alternatively, the Strecker reaction similar to that described by J. Cossy in *Synthesis* 1995, 11, 1368-1370 may be done with TMSCN/HOAc and the resulting mixture of diastereomeric products can be treated with TMSCN in EtOH with heat to equilibrate the mixture so that the major isomer is the desired one. Acylation with a suitable agent like trichloroacetylisocyanate followed by cyclization with methanol/water in a procedure similar to that described by R. Sarges, et. al. in *JOC* 1982, 47 4081-4085 leads to the isolable intermediate iminohydantoin 1A.6 that can be converted directly to the $R^1$ substituted intermediate 1A.7 by heating with a suitable amine. The nitrogen protecting group may then be removed to either give examples of type 1A.8 or alkylated using an alkylating agent and base, like potassium carbonate, to give examples which incorporate an $QR^3$ substituent. Alternatively, $R^3CO_2H$ can be coupled to make an amide bond with 1A.6 which is then reduced with suitable reducing agent such as LAH to give examples of type 1A.9 where Q is a methylene. A third alternative involving reductive amination using a suitable aldehyde or ketone in the presence of borohydride reagent similarly gives examples 1A.9.

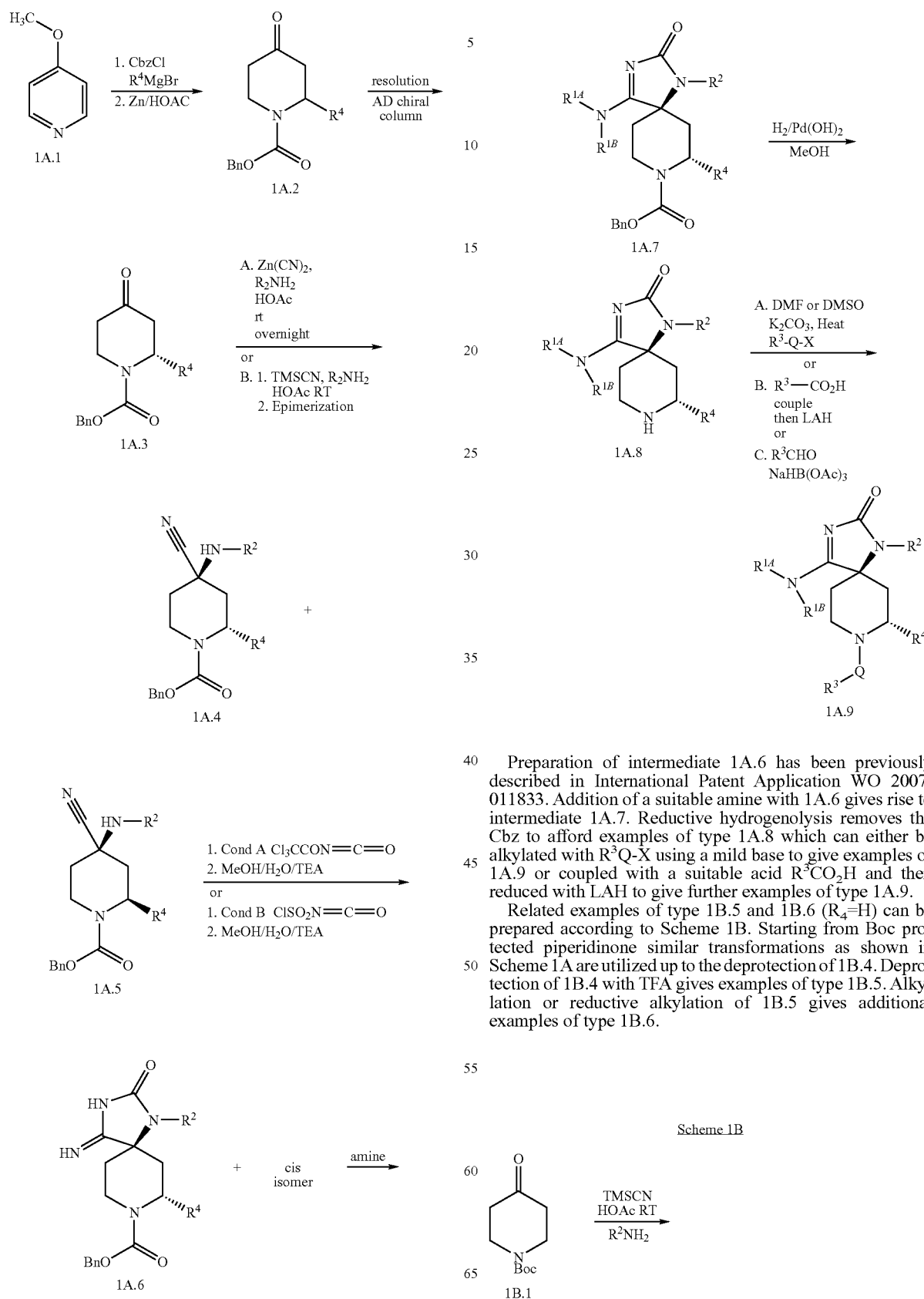

Preparation of intermediate 1A.6 has been previously described in International Patent Application WO 2007/011833. Addition of a suitable amine with 1A.6 gives rise to intermediate 1A.7. Reductive hydrogenolysis removes the Cbz to afford examples of type 1A.8 which can either be alkylated with $R^3Q$-X using a mild base to give examples of 1A.9 or coupled with a suitable acid $R^3CO_2H$ and then reduced with LAH to give further examples of type 1A.9.

Related examples of type 1B.5 and 1B.6 ($R_4$=H) can be prepared according to Scheme 1B. Starting from Boc protected piperidinone similar transformations as shown in Scheme 1A are utilized up to the deprotection of 1B.4. Deprotection of 1B.4 with TFA gives examples of type 1B.5. Alkylation or reductive alkylation of 1B.5 gives additional examples of type 1B.6.

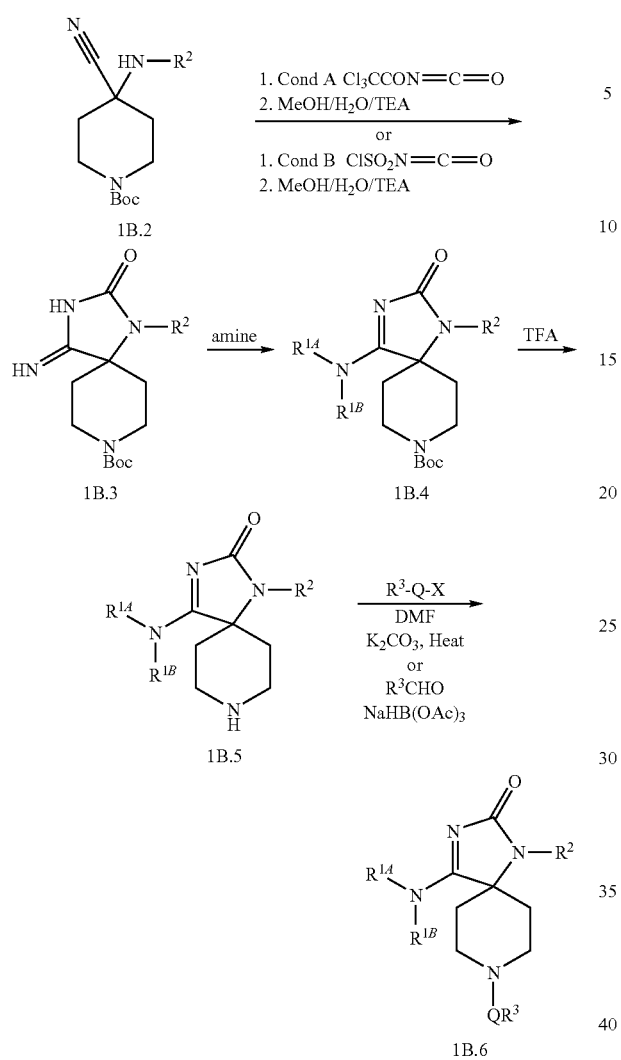

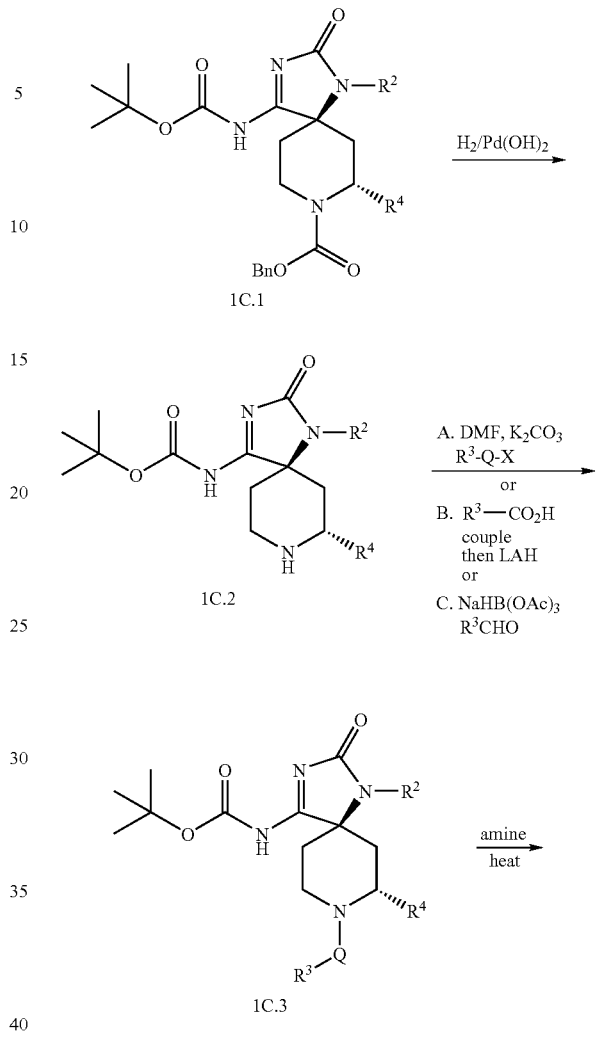

Scheme 1C illustrates the preparation of examples of type 1C.4 starting from Boc protected 1C.1 thus allowing late-stage introduction of various $NR^{1A}R^{1B}$ groups. Orthogonal deprotection of the piperidine benzyl carbamate 1C.1 using standard methods, followed by introduction of $QR^3$ using one of three standard methods (a, b or c) followed by final displacement/deprotection using various $HNR^{1A}R^{1B}$ amines gives examples of type 1C.4.

Scheme 1C

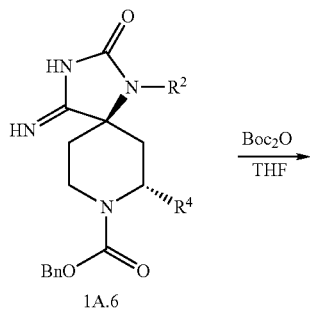

Scheme 2A depicts the formation of compounds of the invention where $X^2$ is CH or substituted carbon. Similar to methods found in R. Jones et al, *Tetrahedron Letters*, 24 (43), 1983, 4751-4754, Strecker reaction on a suitably substituted intermediate gives nitrile 2A-1, which can be acylated to give 2A-2 and then cyclized to 2A-3 by first treatment with a base like NaOMe followed by treatment with a strong aqueous acid like 6 N HCl. 2A-3 may then be treated with a suitable amine to give examples 2A-4 and substituted with a fluorine to give examples 2A-5 upon treatment with a fluorinating agent.

Scheme 2A

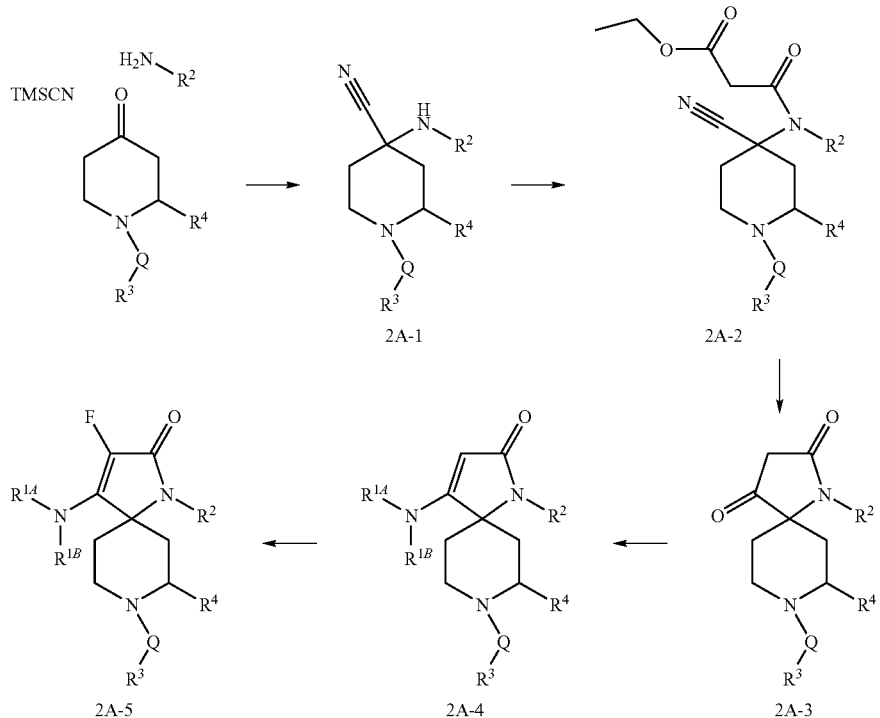

Scheme 3A depicts preparation of examples where X² is optionally substituted carbon Intermediate 2A-3 in the presence of an amine and TMSCN gives Strecker adduct 3A-1. 3A-1 is hydrolyzed to aminoacid 3A-2, then subsequently reduced and oxidized to 3A-3. The aldehyde is then treated with either an organometallic reagent, such as a Grignard or lithium reagent, or an aryl boronic acid in the presence of a Rh(I) catalyst. The resulting alcohol is re-oxidized and closed to the heterocycle 3A-4 with KOCN and heat similar to methods found in Fries, G.; Jassmann, E.; Kowarsch, R.; Bekker, H.; Loew, H. Ger. (East) (1974), 9 pp, GEXXA8 DD 106380 19740612.

Scheme 3A

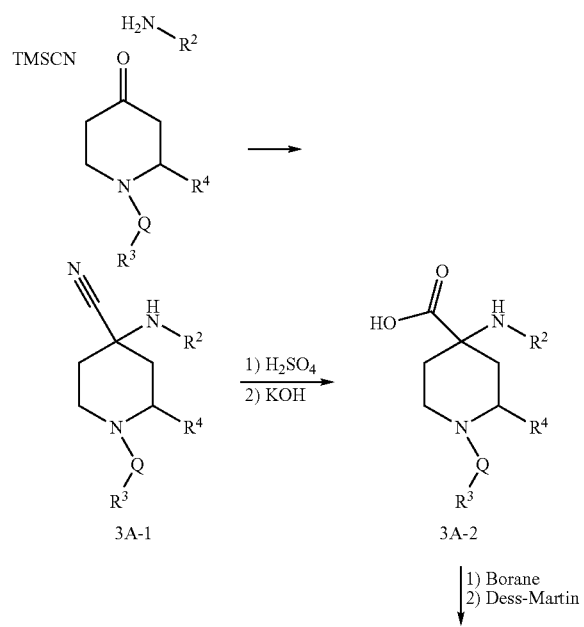

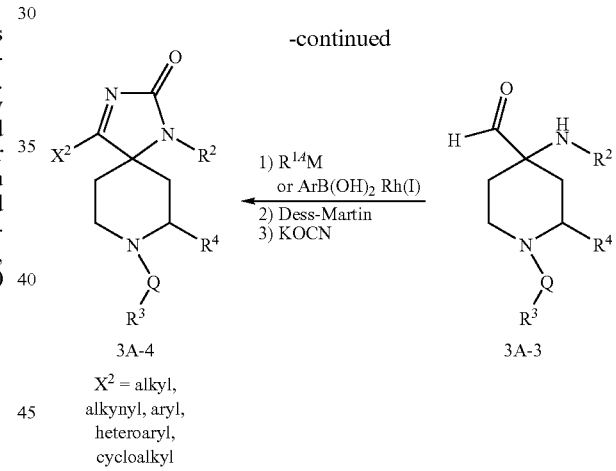

$X^2$ = alkyl, alkynyl, aryl, heteroaryl, cycloalkyl

Scheme 4A depicts a preparation of examples wherein $X^2$ and $X^1$ are optionally carbon or as an alternative to Scheme 2A $X^2=NR^{1A}R^{1B}$ and $X^1$=carbon. Ketoamide 2A-3 (see Scheme 4B for previously described ketoamide preparation in International Patent Application WO 2006044497 and Example 39, step 3 herein) is activated to 4A-1 as either the triflate with Tf$_2$O and a base, to a tosylate using tosyl chloride or to a bromide using PBr$_3$. Intermediate 4A-1 is subsequently treated with various cross-coupling conditions using various aryl, heteroaryl, alkenyl, alkynyl or alkyl organometallic reagents in the presence of a catalytic amounts of a transition metal, such as Ni(0) or Pd(0), to give coupled examples of type 4A-4. In addition intermediates of type 4A-1 can be utilized directly as an alternative access to 2A-4 (4A-2 where $X^2=NR^{1a}NR^{1b}$) via an addition-elimination reaction. Similarly as before, fluoro examples 4A-5 (where $X^2=NR^{1a}NR^{1b}$) can be prepared from examples 4A-4 using a fluorinating agent.

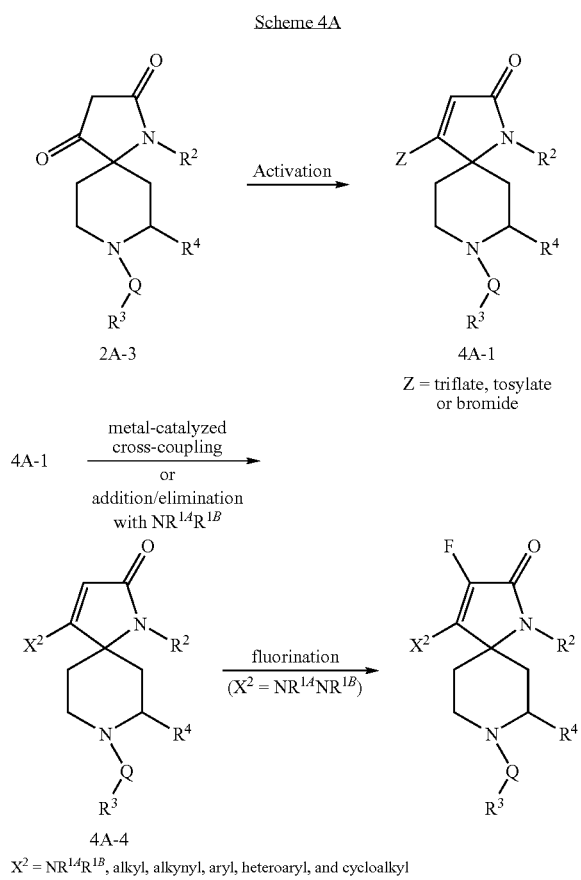

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

The present invention is directed to the use of the compounds of formula (I) disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful for the treatment of mild Alzheimer's Disease, for the treatment of moderate Alzheimer's Disease, or for the treatment of sever Alzheimer's Disease. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

Examples of combinations of the compounds of the present invention with other drugs in either unit dose or kit form include combinations with anti-Alzheimer's agents, for example other beta-secretase inhibitors or gamma-secretase inhibitors; alpha 7 nicotinic agonists, ADAM 10 ligands or activators; glycine transport inhibitors; tau phosphorylation inhibitors; LXR β agonists; ApoE4 conformational modulators; blockers of Aβ oligomer formation; p25/CDK5 inhibitors; HMG-CoA reductase inhibitors; PPAR gamma agonists, such as pioglitazone and rosiglitazone; NK1/NK3 receptor antagonists; NSAID's including ibuprofen; vitamin E; anti-amyloid antibodies, including anti-amyloid humanized monoclonal antibodies; COX-2 inhibitors; anti-inflammatory compounds, such as (R)-flurbiprofen; CB-1 receptor antagonists or CB-1 receptor inverse agonists; antibiotics such as doxycycline and rifampin; N-methyl-D-aspartate (NMDA) receptor antagonists, such as memantine and neramexane; NR2B antagonists; androgen receptor modulators; acetylcholinesterase inhibitors such as galantamine, rivastigmine, donepezil, and tacrine; mGluR5 modulators; growth hormone secretagogues such as ibutamoren, ibutamoren mesylate, and capromorelin; histamine $H_3$ antagonists; AMPA agonists; PDE IV inhibitors; $GABA_A$ inverse agonists; $GABA_A$ α 5 receptor ligands; $GABA_B$ receptor ligands; potassium channel blockers; neuronal nicotinic agonists; mGluR2 modulators; HDAC inhibitors; microtubule affinity regulating kinase (MARK) ligands; P-450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

In the pharmaceutical composition the active compound, which is a compound of the invention, is included in an amount sufficient to produce the desired effect upon the process or condition of diseases. Accordingly, the pharmaceutical compositions of the present invention encompass any composition made by admixing a compound of the invention and a pharmaceutically acceptable carrier.

The carrier may take a wide variety of forms depending on the form of preparation desired for administration, e.g., oral or parenteral (including intravenous). Thus, the pharmaceutical compositions of the invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain a compound of the invention in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a composition of this invention may be prepared by compression or molding, optionally with one or more accessory ingredients or adjuvants. Compressed tablets may be prepared by compressing, in a suitable machine, a compound of the invention in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the compound of the invention.

Compositions for oral use may also be presented as hard gelatin capsules wherein the compound of the invention is mixed with an inert solid diluent, for example, calcium carbonate, calcium phosphate or kaolin, or as soft gelatin capsules wherein the compound of the invention is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the compound of the invention in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound of the invention, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The compositions containing compounds of the invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the invention are indicated, generally satisfactory results are obtained when the compounds of the invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of the compound of the invention that may be combined with the carrier materials to produce a single dosage form will vary depending upon the host treated and the particular mode of administration. For example, a formulation intended for the oral administration to humans may conveniently contain from about 0.005 mg to about 2.5 g of a compound of the invention, compounded with an appropriate and convenient amount of carrier material. Unit dosage forms will generally contain between from about 0.005 mg to about 1000 mg of the compound of the invention, typically 0.005 mg, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is performed using a biotinylated BACE substrate. The Km of the substrate is greater than 100 μM and can not be determined due to the limit of solubility of the substrate. A typical reaction contains approximately 0.1 nM enzyme, 0.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction proceeds for 30 min and is then stopped by the addition of 25 μl, of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 12 concentrations of inhibitors are prepared starting from 100 μM with three fold series dilution. Solutions of the inhibitor in DMSO are included in the reaction mixture (final DMSO concentration is 10%). All experiments are conducted at rt using the standard reaction conditions described above. To determine the IC$_{50}$ of the compound, a four parameter equation is used for curve fitting. The errors in reproducing the dissociation constants are typically less than two-fold.

In particular, the compounds of the following examples had activity in inhibiting the beta-secretase enzyme in the aforementioned assay, generally with an IC$_{50}$ from about 1 nM to 200 μM. Such a result is indicative of the intrinsic activity of the compounds in use as inhibitors of beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Intermediate A: benzyl trans-4-azetidin-1-yl-1-(3-fluorophenyl)-7-methyl-2-oxo-1,3,8-triazaspiro[4.5]dec-3-ene-8-carboxylate

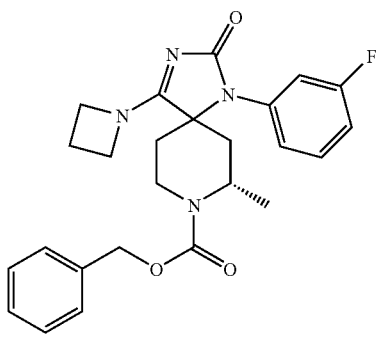

To benzyl trans-4-amino-1-(3-fluorophenyl)-7-methyl-2-oxo-1,3,8-triazaspiro[4.5]dec-3-ene-8-carboxylate (1A.6 previously described in International Patent Application No. PCT/US2006/27594, filed Jul. 14, 2006, 200 mg, 0.48 mmol) was added azetidine (33.0 μl, 0.48 mmol). The neat reaction mixture was sealed and allowed to stir at room temperature for 18 h. The reaction was concentrated in vacuo to yield crude benzyl trans-4-azetidin-1-yl-1-(3-fluorophenyl)-7-methyl-2-oxo-1,3,8-triazaspiro[4.5]dec-3-ene-8-carboxylate. LCMS (M+H) 451.1.

Example 1 trans-4-azetidin-1-yl-1-(3-fluorophenyl)-7-methyl-1,3,8-triazaspiro[4.5]dec-3-en-2-one

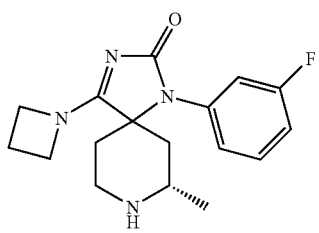

To a solution of benzyl trans-4-azetidin-1-yl-1-(3-fluorophenyl)-7-methyl-2-oxo-1,3,8-triazaspiro[4.5]dec-3-ene-8-carboxylate (220 mg, 0.49 mmol) in methanol (4.0 ml) was added palladium hydroxide (15.0 mg, 20% Pd). The reaction solution was degassed and charged with hydrogen gas. The reaction mixture was allowed to stir at room temperature for 4 h and then filtered over Celite, rinsing with EtOAc. The filtrate was concentrated in vacuo to yield trans-4-azetidin-1-yl-1-(3-fluorophenyl)-7-methyl-1,3,8-triazaspiro[4.5]dec-3-en-2-one (82%). LCMS (M+H) 317.2.

Example 2 trans-4-azetidin-1-yl-1-(3-fluorophenyl)-8-(3-isopropoxybenzyl)-7-methyl-1,3,8-triazaspiro[4.5]dec-3-en-2-one

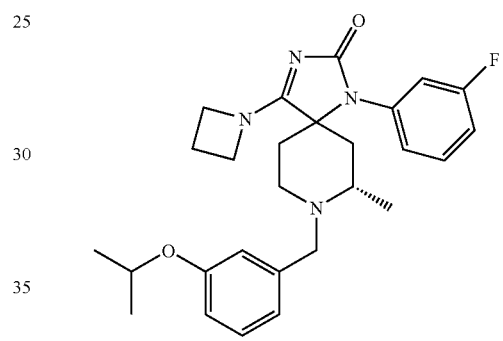

To a solution of trans-4-azetidin-1-yl-1-(3-fluorophenyl)-7-methyl-1,3,8-triazaspiro[4.5]dec-3-en-2-one (100 mg, 0.32 mmol) in DMF (3.0 ml) were added 3-isopropoxybenzyl chloride (58.4 mg, 0.32 mmol), potassium carbonate (218 mg, 1.58 mmol), and sodium iodide (2.4 mg, 0.02 mmol). The reaction was allowed to stir at 70° C. for 1.5 h. The reaction mixture was diluted with water and the product was extracted with EtOAc (3×10 ml). The combined organic layers were washed with 3M LiCl (3×10 ml) and brine, dried over sodium sulfate, and concentrated in vacuo. The crude material was purified via flash chromatography (silica, 0-10% methanol/dichloromethane) to yield trans-4-azetidin-1-yl-1-(3-fluorophenyl)-8-(3-isopropoxybenzyl)-7-methyl-1,3,8-triazaspiro[4.5]dec-3-en-2-one as a white foam (36%). LCMS (M+H) 465.1. $^1$H NMR (400 MHz, CD$_3$OD) δ 7.31 (m, 1H), 7.06 (m, 4H), 6.75 (dd, J=8.0, 2.0 Hz, 1H), 6.62 (m, 2H), 4.75 (br s, 2H), 4.52 (sept, J=6.0 Hz, 1H), 4.25 (br s, 2H), 3.75 (d, J=13.6 Hz, 1H), 3.16 (d, J=13.6 Hz, 1H), 2.58 (m, 1H), 2.51 (quint, J=7.9 Hz, 2H), 2.34 (td, J=13.9, 5.3 Hz, 1H), 2.24 (m, 2H), 2.06 (m, 2H), 1.92 (td, J=12.8, 2.7 Hz, 1H), 1.28 (dd, J=6.2, 1.4 Hz, 6H), 1.16 (d, J=6.4 Hz, 3H).

The following examples were prepared in manner similar to Examples 1 and 2, accordingly to the general Schemes 1A and 1B.

TABLE 1

| | Cyclic Amino Spiropiperidines | | |
|---|---|---|---|
| EX | Structure | Chemical Name | MS M + H |
| 3 | | trans-1-(3-fluorophenyl)-8-(3-isopropoxybenzyl)-7-methyl-4-pyrrolidin-1-yl-1,3,8-triazaspiro[4.5]dec-3-en-2-one | 479 |
| 4 | | trans-1-(3-fluorophenyl)-8-(3-isopropoxybenzyl)-7-methyl-4-(2-methylpyrrolidin-1-yl)-1,3,8-triazaspiro[4.5]dec-3-en-2-one | 493 |
| 5 | | trans-1-(3-fluorophenyl)-8-(3-isopropoxybenzyl)-7-methyl-4-piperidin-1-yl-1,3,8-triazaspiro[4.5]dec-3-en-2-one | 493 |

TABLE 1-continued

Cyclic Amino Spiropiperidines

| EX | Structure | Chemical Name | MS M + H |
|---|---|---|---|
| 6 | 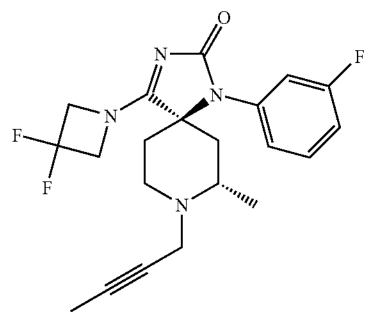 | trans-8-but-2-ynyl-4-(3,3-difluoroazetidin-1-yl)-1-(3-fluorophenyl)-7-methyl-1,3,8-triazaspiro[4.5]dec-3-en-2-one | 405 |
| 7 | 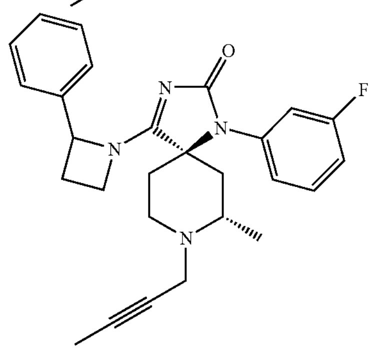 | trans-8-but-2-ynyl-1-(3-fluorophenyl)-7-methyl-4-(2-phenylazetidin-1-yl)-1,3,8-triazaspiro[4.5]dec-3-en-2-one | 445 |
| 8 | 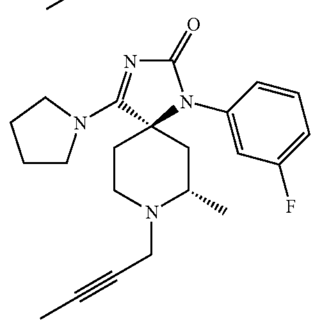 | trans-8-but-2-ynyl-1-(3-fluorophenyl)-7-methyl-4-pyrrolidin-1-yl-1,3,8-triazaspiro[4.5]dec-3-en-2-one | 382 |
| 9 | 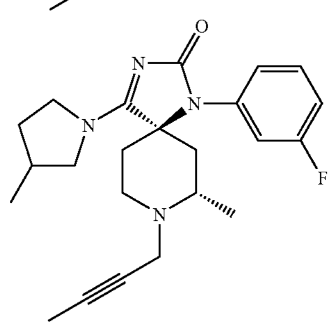 | trans-8-but-2-ynyl-1-(3-fluorophenyl)-7-methyl-4-(3-methylpyrrolidin-1-yl)-1,3,8-triazaspiro[4.5]dec-3-en-2-one | 397 |
| 10 | 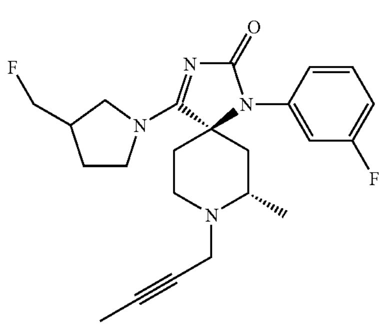 | trans-8-but-2-ynyl-4-[3-(fluoromethyl)pyrrolidin-1-yl]-1-(3-fluorophenyl)-7-methyl-1,3,8-triazaspiro[4.5]dec-3-en-2-one | 415 |

TABLE 1-continued

Cyclic Amino Spiropiperidines

| EX | Structure | Chemical Name | MS M + H |
|---|---|---|---|
| 11 | 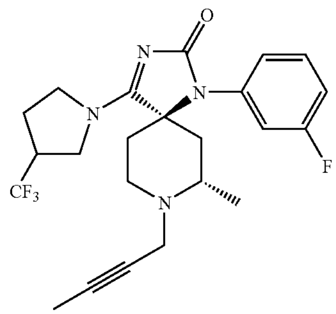 | trans-8-but-2-ynyl-1-(3-fluorophenyl)-7-methyl-4-[3-(trifluoromethyl)pyrrolidin-1-yl]-1,3,8-triazaspiro[4.5]dec-3-en-2-one | 451 |
| 12 | 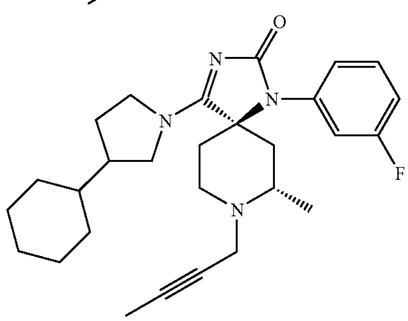 | trans-8-but-2-ynyl-4-(3-cyclohexylpyrrolidin-1-yl)-1-(3-fluorophenyl)-7-methyl-1,3,8-triazaspiro[4.5]dec-3-en-2-one | 465 |
| 13 | 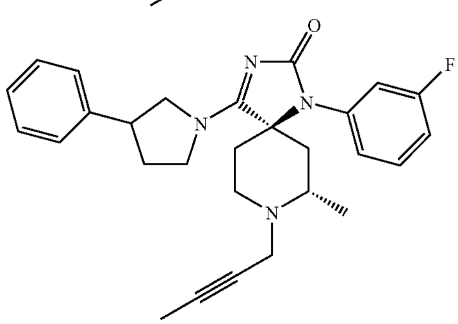 | trans-8-but-2-ynyl-1-(3-fluorophenyl)-7-methyl-4-(3-phenylpyrrolidin-1-yl)-1,3,8-triazaspiro[4.5]dec-3-en-2-one | 459 |
| 14 | 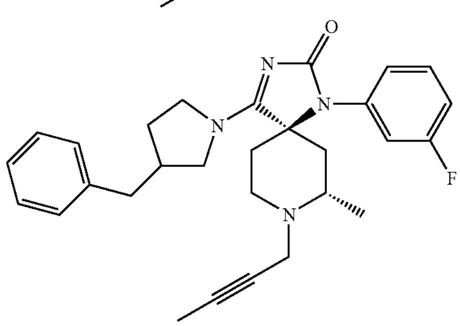 | trans-4-(3-benzylpyrrolidin-1-yl)-8-but-2-ynyl-1-(3-fluorophenyl)-7-methyl-1,3,8-triazaspiro[4.5]dec-3-en-2-one | 473 |
| 15 | 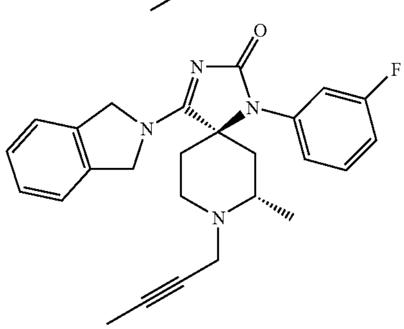 | trans-8-but-2-ynyl-4-(1,3-dihydro-2H-isoindol-2-yl)-1-(3-fluorophenyl)-7-methyl-1,3,8-triazaspiro[4.5]dec-3-en-2-one | 431 |

TABLE 1-continued

Cyclic Amino Spiropiperidines

| EX | Structure | Chemical Name | MS M + H |
|----|-----------|---------------|----------|
| 16 | 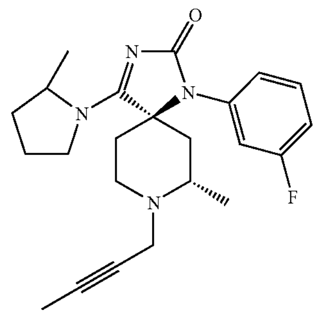 | trans-8-but-2-ynyl-1-(3-fluorophenyl)-7-methyl-4-(2-methylpyrrolidin-1-yl)-1,3,8-triazaspiro[4.5]dec-3-en-2-one | 397 |
| 17 | 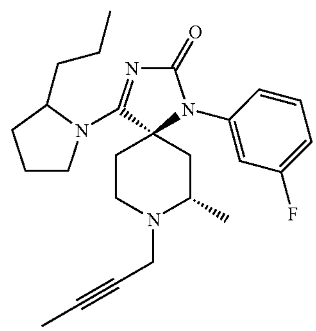 | trans-8-but-2-ynyl-1-(3-fluorophenyl)-7-methyl-4-(2-propylpyrrolidin-1-yl)-1,3,8-triazaspiro[4.5]dec-3-en-2-one | 425 |
| 18 | 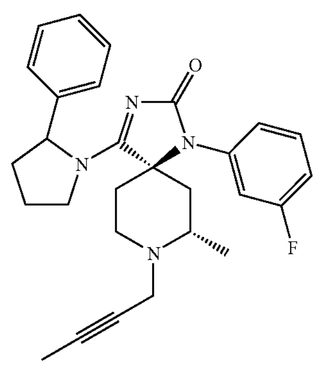 | trans-8-but-2-ynyl-1-(3-fluorophenyl)-7-methyl-4-(2-phenylpyrrolidin-1-yl)-1,3,8-triazaspiro[4.5]dec-3-en-2-one | 573 |
| 19 | 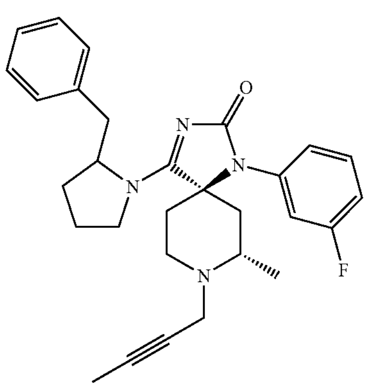 | trans-4-(2-benzylpyrrolidin-1-yl)-8-but-2-ynyl-1-(3-fluorophenyl)-7-methyl-1,3,8-triazaspiro[4.5]dec-3-en-2-one | 474 |

TABLE 1-continued

Cyclic Amino Spiropiperidines

| EX | Structure | Chemical Name | MS M + H |
|---|---|---|---|
| 20 | 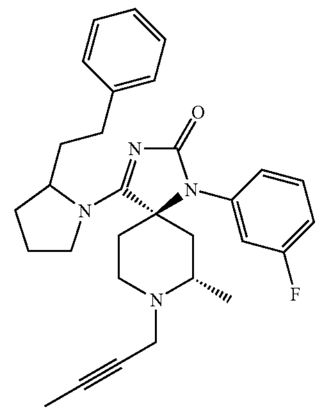 | trans-8-but-2-ynyl-1-(3-fluorophenyl)-7-methyl-4-[2-(2-phenylethyl)pyrrolidin-1-yl]-1,3,8-triazaspiro[4.5]dec-3-en-2-one | 487 |
| 21 | 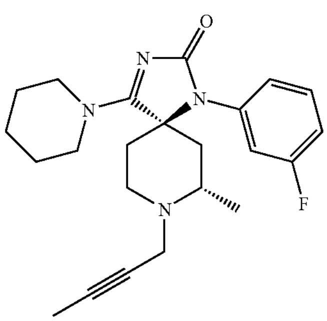 | trans-8-but-2-ynyl-1-(3-fluorophenyl)-7-methyl-4-piperidin-1-yl-1,3,8-triazaspiro[4.5]dec-3-en-2-one | 397 |
| 22 | 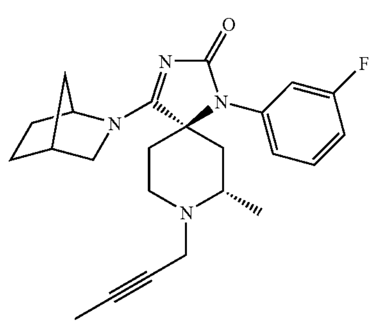 | trans-4-(2-azabicyclo[2.2.1]hept-2-yl)-8-but-2-ynyl-1-(3-fluorophenyl)-7-methyl-1,3,8-triazaspiro[4.5]dec-3-en-2-one | 409 |
| 23 | 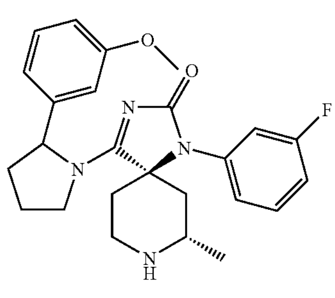 | (5R,7S)-1-(3-fluorophenyl)-4-[2RS-(3-methoxyphenyl)pyrrolidin-1-yl]-7-methyl-1,3,8-triazaspiro[4.5]dec-3-en-2-one | 437 |

TABLE 1-continued

Cyclic Amino Spiropiperidines

| EX | Structure | Chemical Name | MS M + H |
|---|---|---|---|
| 24 | 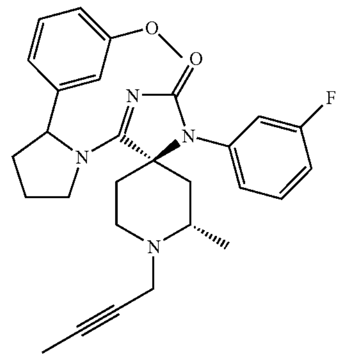 | (5R,7S)-8-but-2-yn-1-yl-1-(3-fluorophenyl)-4-[2RS-(3-methoxyphenyl)pyrrolidin-1-yl]-7-methyl-1,3,8-triazaspiro[4.5]dec-3-en-2-one | 489 |
| 25 | 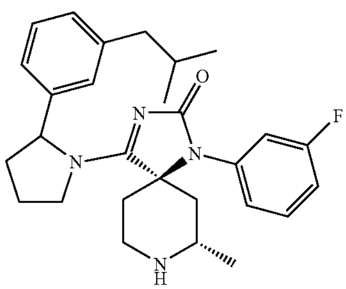 | (5R,7S)-1-(3-fluorophenyl)-4-[2RS-(3-isobutylphenyl)pyrrolidin-1-yl]-7-methyl-1,3,8-triazaspiro[4.5]dec-3-en-2-one | 463 |
| 26 | 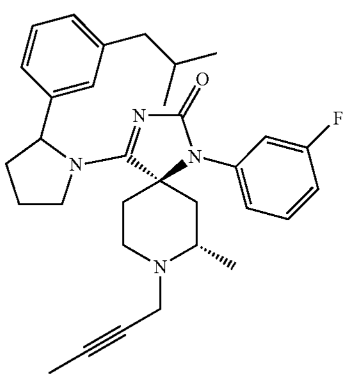 | (5R,7S)-8-but-2-yn-1-yl-1-(3-fluorophenyl)-4-[2RS-(3-isobutylphenyl)pyrrolidin-1-yl]-7-methyl-1,3,8-triazaspiro[4.5]dec-3-en-2-one | 515 |
| 27 | 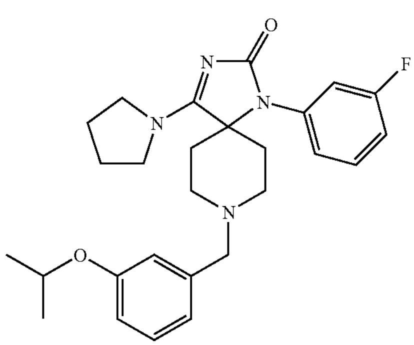 | 1-(3-fluorophenyl)-8-(3-isopropoxybenzyl)-4-pyrrolidin-1-yl-1,3,8-triazaspiro[4.5]dec-3-en-2-one | 465 |

TABLE 1-continued

Cyclic Amino Spiropiperidines

| EX | Structure | Chemical Name | MS M + H |
|---|---|---|---|
| 28 | 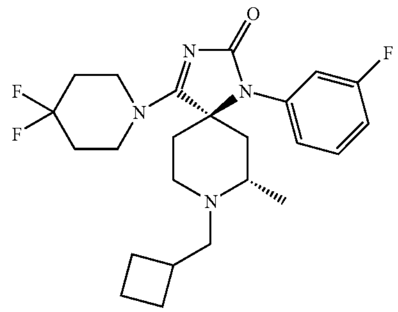 | (5R,7S)-8-(cyclobutylmethyl)-4-(4,4-difluoropiperidin-1-yl)-1-(3-fluorophenyl)-7-methyl-1,3,8-triazaspiro[4.5]dec-3-en-2-one | 449 |
| 29 | 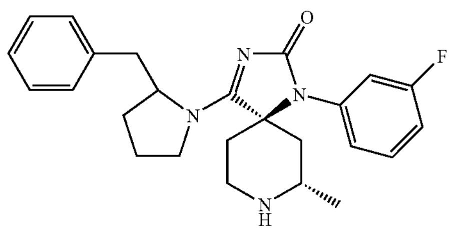 | (5R,7S)-4-(2-benzylpyrrolidin-1-yl)-1-(3-fluorophenyl)-7-methyl-1,3,8-triazaspiro[4.5]dec-3-en-2-one | 421 |
| 30 | 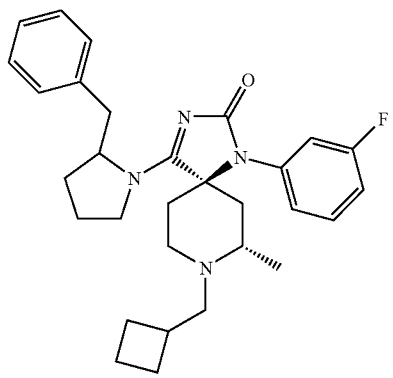 | (5R,7S)-4-(2-benzylpyrrolidin-1-yl)-8-(cyclobutylmethyl)-1-(3-fluorophenyl)-7-methyl-1,3,8-triazaspiro[4.5]dec-3-en-2-one | 489 |

Intermediate B: benzyl (5R,7S)-4-[(tert-butoxycarbonyl)amino]-1-(3-fluorophenyl)-7-methyl-2-oxo-1,3,8-triazaspiro[4.5]dec-3-ene-8-carboxylate

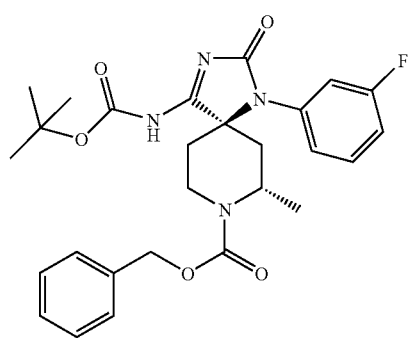

To benzyl trans-4-amino-1-(3-fluorophenyl)-7-methyl-2-oxo-1,3,8-triazaspiro[4.5]dec-3-ene-8-carboxylate (1A.6 previously described in International Patent Application No. WO 2007/011833, 7 g, 17 mmol) in THF (180 mL) was added Boc₂O (4.1 g, 18.8 mmol). The mixture was placed in 70° C. oil bath and allowed to stir for 18 h. The reaction was cooled to rt, concentrated in vacuo and purified using automated SiO₂ flash chromatography (EtOAc/hexanes) to yield 5.6 g of benzyl (5R,7S)-4-[(tert-butoxycarbonyl)amino]-1-(3-fluorophenyl)-7-methyl-2-oxo-1,3,8-triazaspiro[4.5]dec-3-ene-8-carboxylate as a white solid (64%). LCMS (M+H)=411 (M+H-Boc).

Intermediate C: tert-butyl[(5R,7S)-1-(3-fluorophenyl)-7-methyl-2-oxo-1,3,8-triazaspiro[4.5]dec-3-en-4-yl]carbamate

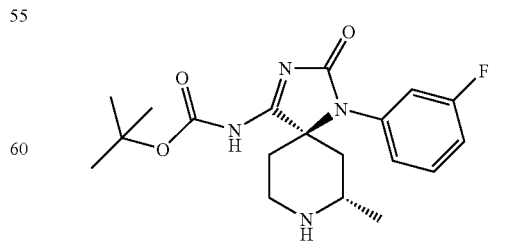

To a flask charged with intermediate B (2.0 g, 3.92 mmol) in degassed MeOH (25 mL) was added Pd(OH)₂ (20% wt 100 mg). The flask was purged with a H₂ balloon and maintained under atm H$_2$ for 6 h. At this time the reaction was filtered over Celite, rinsed with EtOAc and concentrated to dryness to give 1.5 g of tert-butyl[(5R,7S)-1-(3-fluorophenyl)-7-methyl-2-oxo-1,3,8-triazaspiro[4.5]dec-3-en-4-yl]carbamate as a white foam. LCMS (M+H)=277 (M+H-Boc).

Intermediate D: tert-butyl[(5R,7S)-8-(cyclobutylmethyl)-1-(3-fluorophenyl)-7-methyl-2-oxo-1,3,8-triazaspiro[4.5]dec-3-en-4-yl]carbamate

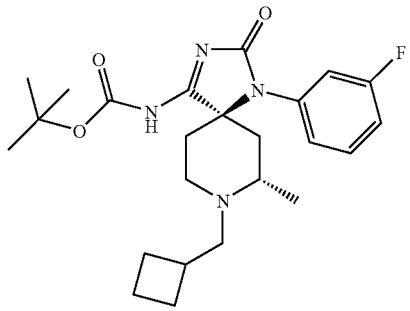

To a solution of intermediate C (1.45 g, 3.85 mmol) and cyclobutane carboxaldehyde (0.97 g, 11.6 mmol prepared from alcohol using TPAP/NMO) in DCM (60 mL) at 0° C. was added NaHB(OAc)$_3$ (1.23 g, 5.8 mmol). The mixture was allowed to slowly warm to rt and stir for 18 h. The mixture was diluted with aq. NaHCO$_3$ and DCM. The organic layer was isolated, washed sequentially with water and brine, dried with Na$_2$SO$_4$ and concentrated to dryness to give 2.6 g of crude material. Purification using automated SiO$_2$ chromatography (MeOH/DCM) provided 1.5 g of desired tert-butyl[(5R,7S)-8-(cyclobutylmethyl)-1-(3-fluorophenyl)-7-methyl-2-oxo-1,3,8-triazaspiro[4.5]dec-3-en-4-yl]carbamate as a white foam. LCMS (M+H)=445.

Example 31

Trans-8-(cyclobutylmethyl)-1-(3-fluorophenyl)-7-methyl-4-[2-(2-methylbenzyl)pyrrolidin-1-yl]-1,3,8-triazaspiro[4.5]dec-3-en-2-one

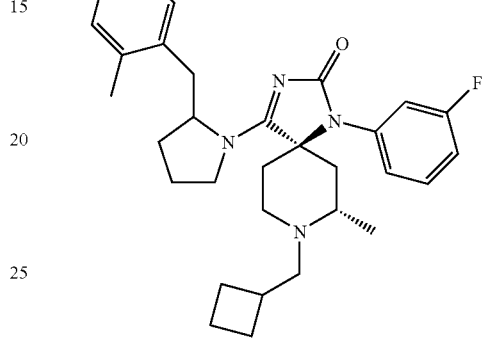

To a solution of of Intermediate D (184 mg, 0.41 mmol) in 0.5 mL of dimethylacetamide in a scintillation vial was added 2-(2-methylbenzyl)pyrrolidine (218 mg, 1.24 mmol). The vessel was sealed and placed in a 110° C. oil bath and stirred for 2 d. The reaction was cooled to rt, filtered over 0.45 micron frit and purified by RP-HPLC. The product fractions were freeze-dried to give 10 mg of titled compound. LCMS (M+H)=503.

The following examples were prepared in manner similar to Example 31 using intermediate D according to the general Scheme 1C.

TABLE 2

| | Cyclic Amino Spiropiperidines | | |
|---|---|---|---|
| EX | Structure | Chemical Name | MS M + H |
| 32 | | trans-4-[2-(3-chlorobenzyl)pyrrolidin-1-yl]-8-(cyclobutylmethyl)-1-(3-fluorophenyl)-7-methyl-1,3,8-triazaspiro[4.5]dec-3-en-2-one | 524 |

TABLE 2-continued

Cyclic Amino Spiropiperidines

| EX | Structure | Chemical Name | MS M + H |
|---|---|---|---|
| 33 | 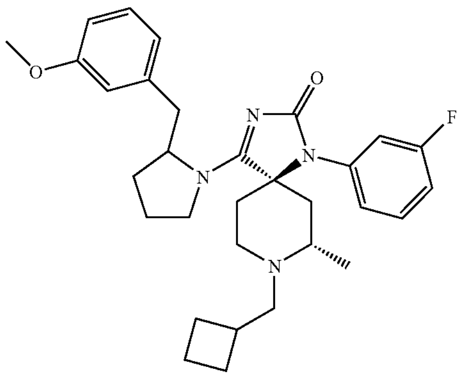 | trans-8-(cyclobutylmethyl)-1-(3-fluorophenyl)-4-[2-(3-methoxybenzyl)pyrrolidin-1-yl]-7-methyl-1,3,8-triazaspiro[4.5]dec-3-en-2-one | 519 |
| 34 | 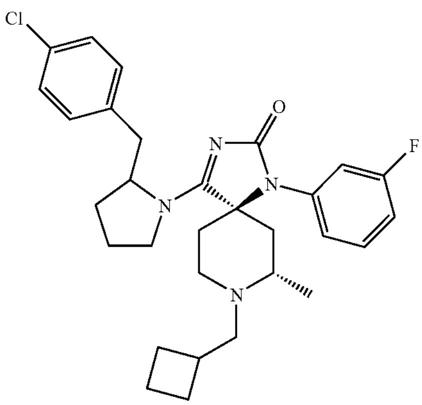 | trans-4-[2-(4-chlorobenzyl)pyrrolidin-1-yl]-8-(cyclobutylmethyl)-1-(3-fluorophenyl)-7-methyl-1,3,8-triazaspiro[4.5]dec-3-en-2-one | 524 |
| 35 | 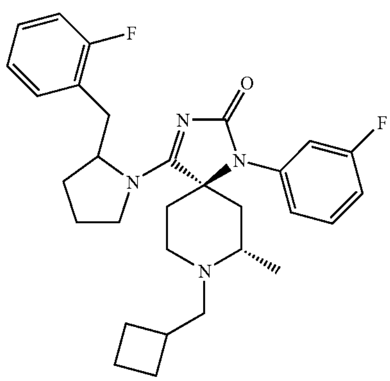 | trans-8-(cyclobutylmethyl)-4-[2-(2-fluorobenzyl)pyrrolidin-1-yl]-1-(3-fluorophenyl)-7-methyl-1,3,8-triazaspiro[4.5]dec-3-en-2-one | 507 |
| 36 | 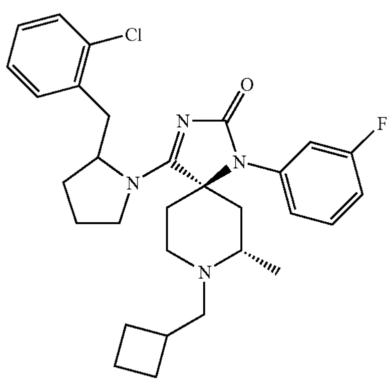 | (5R,7S)-4-[2-(2-chlorobenzyl)pyrrolidin-1-yl]-8-(cyclobutylmethyl)-1-(3-fluorophenyl)-7-methyl-1,3,8-triazaspiro[4.5]dec-3-en-2-one | 524 |

The following examples in Table 3 were prepared in a manner similar to Example 2 Scheme 1A using intermediate 1A.6 and various alternate H₂NR₂ groups according to the general Scheme 1C and using alkylation conditions similar to Intermediate D (method C Scheme 1A).

To trans-benzyl-4-amino-1-(3-fluorophenyl)-7-methyl-2-oxo-1,3,8-triazaspiro[4.5]dec-3-ene-8-carboxylate (1A.6 previously described in International Patent Application No. WO 2007/011833, 19 g, 51.7 mmol) in MeOH (200 mL) was added 20% Pd/C (22 g, 10 mmol). The mixture was placed

TABLE 3

Cyclic Amino Spiropiperidines

| EX | Structure | Chemical Name | MS M + H |
|---|---|---|---|
| 37 | 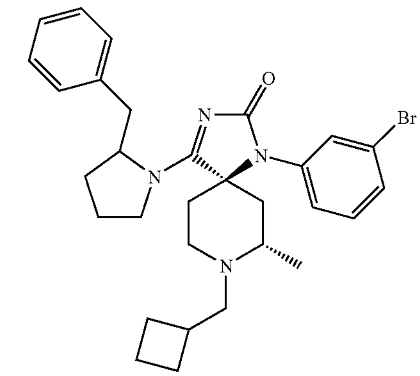 | (5R,7S)-4-(2-benzylpyrrolidin-1-yl)-1-(3-bromophenyl)-8-(cyclobutylmethyl)-7-methyl-1,3,8-triazaspiro[4.5]dec-3-en-2-one | 550 |
| 38 | 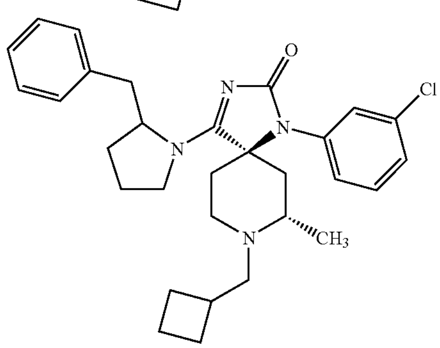 | (5R,7S)-4-(2-benzylpyrrolidin-1-yl)-1-(3-chlorophenyl)-8-(cyclobutylmethyl)-7-methyl-1,3,8-triazaspiro[4.5]dec-3-en-2-one | 506 |

Example 39

Trans-8-(cyclobutylmethyl)-1-(3-fluorophenyl)-7-methyl-4-phenyl-1,8-diazaspiro[4.5]dec-3-en-2-one

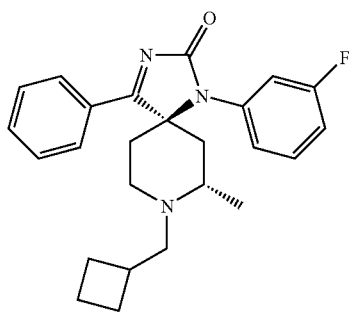

Step 1. Cbz removal of Strecker 1A.6. Trans-4-[(3-fluorophenyl)amino]-2-methylpiperidine-4-carbonitrile

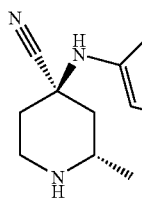

under atmospheric H₂ and stirred at rt overnight. The reaction was filtered over Celite, the filtrate concentrated and purified using SiO₂ flash chromatography using 5% EtOAc/DCM to remove unreacted starting material and then eluted with 10% MeOH/DCM to give 9.96 g of trans-4-[(3-fluorophenyl)amino]-2-methylpiperidine-4-carbonitrile and 5.95 g of the related cis diastereomer. LCMS (M+H)=234.

Step 2. Reductive alkylation. Trans-1-(cyclobutylmethyl)-4-[(3-fluorophenyl)amino]-2-methylpiperidine-4-carbonitrile

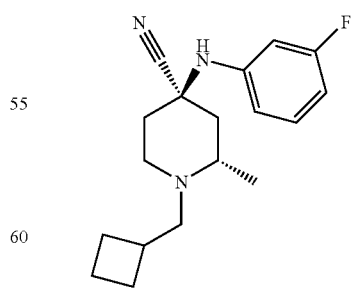

To a DCE (142 mL) solution of trans-4-[(3-fluorophenyl)amino]-2-methylpiperidine-4-carbonitrile from step 1 (9.96 g, 42.7 mmol) was added acetic acid (2.44 mL, 42.7 mmol). Cyclobutanecarboxaldehyde (14.3 g, 85 mmol) was added and the reaction stirred at rt for 10 min followed by addition of NaHB(OAc)₃ (13.6 g, 64 mmol). After stirring for 30 min. the mixture was extracted with DCM and washed with 1N NaOH. The combined organic extracts were dried over Na₂SO₄ and the solvent evaporated under reduced pressure to give 8.0 g of the titled intermediate. The product was used without further purification. LCMS (M+H)=303.

Step 3. Cyclization to ketoamide. Trans-8-(cyclobutylmethyl)-1-(3-fluorophenyl)-7-methyl-1,8-diazaspiro[4.5]decane-2,4-dione

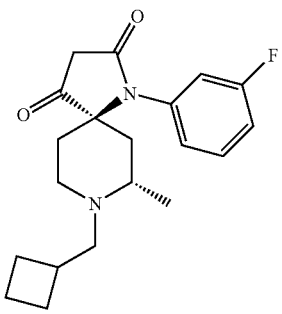

To a DCM (50 mL) solution of trans-1-(cyclobutylmethyl)-4-[(3-fluorophenyl)amino]-2-methylpiperidine-4-carbonitrile (8.0 g, 26.5 mmol) from step 2 was added sequentially ethyl malonyl chloride (5.0 mL, 39 mmol) dropwise, TEA (5.55 mL, 39.8 mmol) and DMAP (162 mg, 1.3 mmol). The reaction stirred at rt overnight. The mixture was extracted with DCM and washed with brine. The combined organic extracts were dried over Na₂SO₄, filtered and the solvent evaporated under reduced pressure. The mixture was purified by SiO₂ column chromatography (5% MeOH/DCM) and the product fractions combined and evaporated to give an orange oil (11 g). The resulting material was re-dissolved in MeOH (15 mL) and NaOMe (1.71 g, 31.8 mmol) added. The reaction was stirred at rt for 1 h and the mixture concentrated to dryness under reduced pressure. To the crude mixture 6M HCl (60 mL) was added and the reaction refluxed for 4 h. The mixture was cooled to rt, poured onto ice and made neutral using KOH pellet addition. The mixture was extracted repeatedly with EtOAc followed by DCM. The organic phases were dried over Na₂SO₄ and concentrated to dryness. The crude was purified by SiO₂ chromatography (5% MeOH/DCM) to give the title product as a light oil upon drying in vacuo. LCMS (M+H)=345.

Step 4. Formation of Tosylate. Trans-8-(cyclobutylmethyl)-1-(3-fluorophenyl)-7-methyl-2-oxo-1,8-diazaspiro[4.5]dec-3-en-4-yl-4-methylbenzenesulfonate.

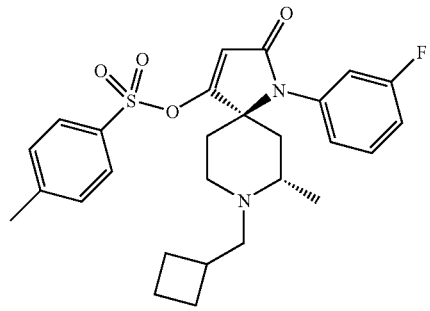

Trans-8-(cyclobutylmethyl)-1-(3-fluorophenyl)-7-methyl-1,8-diazaspiro[4.5]decane-2,4-dione ketoamide from step 3 (2.3 g, 6.7 mmol) was dissolved in DCM (15 mL). Pyridine (0.52 g, 6.7 mmol) was added followed by tosyl chloride (1.3 g, 6.7 mmol). The reaction was stirred 30 min. and washed with 1N NaOH (15 mL) added. The aqueous layers were extracted with DCM (2×15 mL). The organic extracts were combined and dried over Na₂SO₄. The solvent was evaporated under reduced pressure. The residue was purified by SiO₂ column chromatography (2% MeOH/DCM) and the product fractions combined and concentrated to give a light pink powder. LCMS (M+H)=499.

Step 5. Ni-catalyzed cross coupling to give Example 39 Trans-8-(cyclobutylmethyl)-1-(3-fluorophenyl)-7-methyl-2-oxo-1,8-diazaspiro[4.5]dec-3-en-4-yl 4-methylbenzenesulfonate (200 mg, 0.40 mmol) and 1,2-bis(diphenylphosphino)ethane nickel(II)chloride (42 mg, 0.08 mmol) were dissolved in degassed THF (5.0 mL). Phenylzinc iodide (1.20 mL, 2.0 M 0.60 mmol) was added via syringe. The mixture was heated to 55° C. and stirred overnight. At this time 3 equiv of additional 1,2-bis(diphenylphosphino)ethane nickel(II) chloride and 3 equiv phenylzinc iodide was added. The mixture was cooled to rt and diluted with water and DCM. The organic phase was isolated, washed with brine and dried over Na₂SO₄. The solvent was removed under reduced pressure and the crude product purified by RP-HPLC. The product fractions were concentrated and submitted to further purification using an AD Chiral Column. Two major peaks eluted and were shown to contain material consistent for product based on M+H (one of which was presumed to be the trans diastereomers, the other cis). LCMS (M+H)=405.

Compounds in Tables 1-3 having a basic group or acidic group are depicted and named as the free base acid. Depending on the reaction and purification conditions, various compounds in Tables 1-3 having a basic group were isolated in either the free base form, or as a salt (such as HCl salt), or in both free base and salt forms.

The following abbreviations are used throughout the text:
Me: methyl
Et: ethyl
Bu: butyl
t-Bu: tert-butyl
i-Bu: iso-butyl
Pr: propyl
i-Pr: iso-propyl
Ac: acetyl
Bn: benzyl
Ar: aryl
Ph: phenyl
Boc: tert-butyloxycarbonyl
TFA: trifluoro acetic acid
THF: tetrahydrofuran
Cbz: carbobenzyloxy
TMS: trimethyl silyl
TPAP: tetrapropylammonium perruthenate
NMO: N-methylmorpholine-N-oxide
DMAP: dimethylaminopyridine
LAH: lithium aluminum hydride
TEA: triethylamine
DMF: N,N'-dimethylformamide
DMSO: dimethylsulfoxide
EDTA: ethyledene diamine tetraacetic acid
CHAPS: 3-[(3-cholamidopropyl)dimethylammonio]-2-hydroxy-1-propanesulfonate
BSA: bovine serum albumin
Ac: acetyl
aq: aqueous rt: room temperature
h: hours
min: minute While the invention has been described and illustrated with reference to certain embodiments thereof, those skilled in the art will appreciate that various changes, modifications and substitutions can be made therein without departing from the spirit and scope of the invention.

What is claimed is:

1. A compound of formula (I):

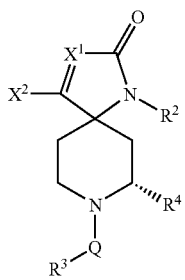

(I)

wherein:

$X^1$ is selected from the group consisting of
(1) N;

$X^2$ is selected from the group consisting of
(1) —$NR^{1A}R^{1B}$,
wherein $R^{1A}$ and $R^{1B}$ are linked together with the nitrogen to which they are attached to form a ring structure comprising three to nine ring carbon atoms, wherein one or more of said ring carbon atoms is optionally substituted with one or more
(a) halo,
(b) —OH,
(c) —CN,
(d) —$C_{1-10}$ alkyl
(e) —$C_{3-12}$ cycloalkyl,
(f) —O—$C_{1-10}$ alkyl, or
(g) —$C_{0-6}$ alkyl-aryl,
wherein said alkyl, cycloalkyl or aryl moiety is optionally substituted with one or more
(i) halo,
(ii) —OH,
(iii) —CN,
(iv) —$C_{1-6}$ alkyl,
(v) —$C_{2-6}$ alkenyl,
(vi) —O—$C_{1-6}$ alkyl, or
(vii) —$C_{1-6}$ haloalkyl,
(2) —$C_{1-10}$ alkyl
(3) —$C_{3-12}$ cycloalkyl,
(4) —$C_{1-10}$ alkynyl,
(5) aryl, and
(6) heteroaryl,
wherein said $X^2$ alkyl, cycloalkyl, aryl or alkynyl moiety is optionally substituted with one or more
(a) —$C_{1-10}$ alkyl,
(b) halo,
(c) —OH,
(d) —CN,
(e) —O—$C_{1-10}$ alkyl, or
(f) —$C_{0-6}$ alkyl-aryl;

$R^2$ is phenyl, wherein said phenyl $R^2$ moiety is optionally substituted with one or more:
(a) halo,
(b) —OH,
(c) —CN,
(d) —$C_{1-10}$ alkyl
(e) —$C_{3-12}$ cycloalkyl,
(f) —O—$C_{1-10}$ alkyl,
(g) —$C_{0-6}$ alkyl-aryl,
(h) —$C_{0-6}$ alkyl-heteroaryl, or
(o) a non-aromatic heterocyclic group having 4 to 8 ring atoms, wherein one ring atom is a heteroatom selected from the group consisting of nitrogen and oxygen,
and said alkyl, cycloalkyl, aryl, heteroaryl and heterocyclic moiety is optionally substituted with one or more
(i) halo,
(ii) —OH,
(iii) —CN,
(iv) —$C_{1-10}$ alkyl, wherein said alkyl is optionally substituted with one or more halo,
(v) —O—$C_{1-10}$ alkyl, wherein said alkyl is optionally substituted with one or more halo, or
(vi) —$SO_2C_{1-3}$ alkyl, Q is a bond or —$C_{1-6}$ alkyl, wherein said alkyl is optionally substituted with one or more
(a) halo,
(b) —OH,
(c) —CN,
(d) —$C_{1-10}$ alkyl, or
(e) —O—$C_{1-10}$ alkyl;

$R^3$ is selected from the group consisting of
(1) hydrogen,
(2) —$C_{1-10}$ alkyl,
(3) —$C_{2-10}$ alkenyl,
(4) —$C_{3-12}$ cycloalkyl, and
(5) phenyl,
wherein said alkyl, cycloalkyl, alkenyl, or phenyl $R^3$ moiety is optionally substituted with one or more
(a) halo,
(b) —OH,
(c) —CN,
(d) —$C_{1-10}$ alkyl,
(e) —$C_{2-10}$ alkenyl,
(f) —$C_{3-12}$ cycloalkyl,
(g) —O—$C_{3-12}$ cycloalkyl, or
(h) —O—$C_{1-10}$ alkyl;
provided that when Q is a bond then $R^3$ is hydrogen; and $R^4$ is selected from the group consisting of
(1) hydrogen, and
(2) —$C_{1-10}$ alkyl;
or a pharmaceutically acceptable salt thereof.

2. A compound of claim 1, wherein $X^2$ is $NR^{1A}R^{1B}$, wherein $R^{1A}$ and $R^{1B}$ are linked together with the nitrogen to which they are attached to form a ring structure comprising three to nine ring carbon atoms, wherein one or more of said ring carbon atoms is optionally substituted with one or more
(a) halo,
(b) —$C_{1-10}$ alkyl
(c) —$C_{3-12}$ cycloalkyl,
(d) —O—$C_{1-10}$ alkyl, or
(e) alkyl-aryl,
wherein said alkyl, cycloalkyl or aryl moiety is optionally substituted with one or more
(i) halo,
(ii) —$C_{1-6}$ alkyl,
(iii) —O—$C_{1-6}$ alkyl, or
(iv) —$C_{1-6}$ haloalkyl.

3. A compound of claim 1, wherein $R^2$ is phenyl, which is optionally substituted with one or more
(a) halo,
(b) —OH,
(c) —CN,
(d) —$C_{1-10}$ alkyl, (e) —C$_{3-12}$ cycloalkyl,
(f) —O—C$_{1-10}$ alkyl, or
(g) —C$_{0-6}$ alkyl-aryl, wherein said aryl is optionally substituted with one or more
  (i) halo,
  (ii) —OH, or
(h) —C$_{0-6}$ alkyl-heteroaryl.

4. A compound of claim 1, wherein Q is —CH$_2$—, and R$^3$ is selected from the group consisting of
(1) —C$_{1-10}$ alkyl,
(2) —C$_{3-12}$ cycloalkyl, and
(3) phenyl,
wherein said alkyl, cycloalkyl, or phenyl R$^3$ moiety is optionally substituted with one or more
  (a) halo,
  (b) —OH,
  (c) —C$_{1-10}$ alkyl,
  (d) —C$_{3-12}$ cycloalkyl, or
  (e) —O—C$_{1-10}$ alkyl.

5. A compound of claim 1, wherein R$^4$ is —C$_{1-10}$ alkyl.

6. A compound of claim 5, wherein R$^4$ is methyl.

7. A compound of claim 1, wherein the compound of formula (I) is a compound of formula (II):

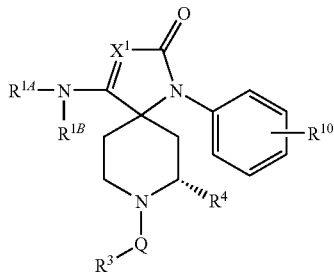

wherein R$^{10}$ is selected from the group consisting of
(a) halo,
(b) —OH,
(c) —CN,
(d) —C$_{1-10}$ alkyl
(e) —C$_{3-12}$ cycloalkyl,
(f) —O—C$_{1-10}$ alkyl,
(g) —C$_{0-6}$ alkyl-aryl, wherein said aryl is optionally substituted with one or more
  (i) halo,
  (ii) —OH,
  (iii) —CN,
  (iv) —C$_{1-6}$ alkyl,
  (v) —OC$_{1-6}$ alkyl,
  (vi) —C$_{1-6}$ haloalkyl,
  (vii) —SO$_2$C$_{1-3}$ alkyl,
(h) —C$_{0-6}$ alkyl-heteroaryl, and
(m) a non-aromatic heterocyclic group having 4 to 8 ring atoms, wherein one ring atom is a heteroatom selected from the group consisting of nitrogen and oxygen, and said alkyl, cycloalkyl and heteroaryl moiety is optionally substituted with one or more
  (i) halo,
  (ii) —OH,
  (iii) —CN,
  (iv) —C$_{1-10}$ alkyl,
  (v) —O—C$_{1-10}$ alkyl, and
  (vi) —SO$_2$C$_{1-3}$ alkyl,
or a pharmaceutically acceptable salt thereof.

8. A compound of claim 7, wherein R$^{1A}$ and R$^{1B}$ are linked together with the nitrogen to which they are attached to form a ring structure comprising four to nine ring carbon atoms, wherein one or more of said ring carbon atoms is optionally substituted with one or more
(a) halo,
(b) —C$_{1-10}$ alkyl
(c) —C$_{3-12}$ cycloalkyl,
(d) —O—C$_{1-10}$ alkyl, or
(e) alkyl-aryl,
wherein said alkyl, cycloalkyl or aryl moiety is optionally substituted with one or more
  (i) halo,
  (ii) —C$_{1-6}$ alkyl,
  (iii) —O—C$_{0-6}$ alkyl, or
  (iv) —C$_6$ haloalkyl.

9. A compound of claim 1, which is selected from the group consisting of
trans-4-azetidin-1-yl-1-(3-fluorophenyl)-7-methyl-1,3,8-triazaspiro[4.5]dec-3-en-2-one;
trans-4-azetidin-1-yl-1-(3-fluorophenyl)-8-(3-isopropoxybenzyl)-7-methyl-1,3,8-triazaspiro[4.5]dec-3-en-2-one;
trans-1-(3-fluorophenyl)-8-(3-isopropoxybenzyl)-7-methyl-4-pyrrolidin-1-yl-1,3,8-triazaspiro[4.5]dec-3-en-2-one;
trans-1-(3-fluorophenyl)-8-(3-isopropoxybenzyl)-7-methyl-4-(2-methylpyrrolidin-1-yl)-1,3,8-triazaspiro[4.5]dec-3-en-2-one;
trans-1-(3-fluorophenyl)-8-(3-isopropoxybenzyl)-7-methyl-4-piperidin-1-yl-1,3,8-triazaspiro[4.5]dec-3-en-2-one;
trans-8-but-2-ynyl-4-(3,3-difluoroazetidin-1-yl)-1-(3-fluorophenyl)-7-methyl-1,3,8-triazaspiro[4.5]dec-3-en-2-one;
trans-8-but-2-ynyl-1-(3-fluorophenyl)-7-methyl-4-(2-phenylazetidin-1-yl)-1,3,8-triazaspiro[4.5]dec-3-en-2-one;
trans-8-but-2-ynyl-1-(3-fluorophenyl)-7-methyl-4-pyrrolidin-1-yl-1,3,8-triazaspiro[4.5]dec-3-en-2-one;
trans-8-but-2-ynyl-1-(3-fluorophenyl)-7-methyl-4-(3-methylpyrrolidin-1-yl)-1,3,8-triazaspiro[4.5]dec-3-en-2-one;
trans-8-but-2-ynyl-4-[3-(fluoromethyl)pyrrolidin-1-yl]-1-(3-fluorophenyl)-7-methyl-1,3,8-triazaspiro[4.5]dec-3-en-2-one;
trans-8-but-2-ynyl-1-(3-fluorophenyl)-7-methyl-4-[3-(trifluoromethyl)pyrrolidin-1-yl]-1,3,8-triazaspiro[4.5]dec-3-en-2-one;
trans-8-but-2-ynyl-4-(3-cyclohexylpyrrolidin-1-yl)-1-(3-fluorophenyl)-7-methyl-1,3,8-triazaspiro[4.5]dec-3-en-2-one;
trans-8-but-2-ynyl-1-(3-fluorophenyl)-7-methyl-4-(3-phenylpyrrolidin-1-yl)-1,3,8-triazaspiro[4.5]dec-3-en-2-one;
trans-4-(3-benzylpyrrolidin-1-yl)-8-but-2-ynyl-1-(3-fluorophenyl)-7-methyl-1,3,8-triazaspiro[4.5]dec-3-en-2-one;
trans-8-but-2-ynyl-4-(1,3-dihydro-2H-isoindol-2-yl)-1-(3-fluorophenyl)-7-methyl-1,3,8-triazaspiro[4.5]dec-3-en-2-one;
trans-8-but-2-ynyl-1-(3-fluorophenyl)-7-methyl-4-(2-methylpyrrolidin-1-yl)-1,3,8-triazaspiro[4.5]dec-3-en-2-one;
trans-8-but-2-ynyl-1-(3-fluorophenyl)-7-methyl-4-(2-propylpyrrolidin-1-yl)-1,3,8-triazaspiro[4.5]dec-3-en-2-one;

trans-8-but-2-ynyl-1-(3-fluorophenyl)-7-methyl-4-(2-phenylpyrrolidin-1-yl)-1,3,8-triazaspiro[4.5]dec-3-en-2-one;

trans-4-(2-benzylpyrrolidin-1-yl)-8-but-2-ynyl-1-(3-fluorophenyl)-7-methyl-1,3,8-triazaspiro[4.5]dec-3-en-2-one;

trans-8-but-2-ynyl-1-(3-fluorophenyl)-7-methyl-4-[2-(2-phenylethyl)pyrrolidin-1-yl]-1,3,8-triazaspiro[4.5]dec-3-en-2-one;

trans-8-but-2-ynyl-1-(3-fluorophenyl)-7-methyl-4-piperidin-1-yl-1,3,8-triazaspiro[4.5]dec-3-en-2-one;

trans-4-(2-azabicyclo[2.2.1]hept-2-yl)-8-but-2-ynyl-1-(3-fluorophenyl)-7-methyl-1,3,8-triazaspiro[4.5]dec-3-en-2-one;

(5R,7S)-1-(3-fluorophenyl)-4-[2RS-(3-methoxyphenyl)pyrrolidin-1-yl]-7-methyl-1,3,8-triazaspiro[4.5]dec-3-en-2-one;

(5R,7S)-8-but-2-yn-1-yl-1-(3-fluorophenyl)-4-[2RS-(3-methoxyphenyl)pyrrolidin-1-yl]-7-methyl-1,3,8-triazaspiro[4.5]dec-3-en-2-one;

(5R,7S)-1-(3-fluorophenyl)-4-[2RS-(3-isobutylphenyl)pyrrolidin-1-yl]-7-methyl-1,3,8-triazaspiro[4.5]dec-3-en-2-one;

(5R,7S)-8-but-2-yn-1-yl-1-(3-fluorophenyl)-4-[2RS-(3-isobutylphenyl)pyrrolidin-1-yl]-7-methyl-1,3,8-triazaspiro[4.5]dec-3-en-2-one;

1-(3-fluorophenyl)-8-(3-isopropoxybenzyl)-4-pyrrolidin-1-yl-1,3,8-triazaspiro[4.5]dec-3-en-2-one;

(5R,7S)-8-(cyclobutylmethyl)-4-(4,4-difluoropiperidin-1-yl)-1-(3-fluorophenyl)-7-methyl-1,3,8-triazaspiro[4.5]dec-3-en-2-one;

(5R,7S)-4-(2-benzylpyrrolidin-1-yl)-1-(3-fluorophenyl)-7-methyl-1,3,8-triazaspiro[4.5]dec-3-en-2-one;

(5R,7S)-4-(2-benzylpyrrolidin-1-yl)-8-(cyclobutylmethyl)-1-(3-fluorophenyl)-7-methyl-1,3,8-triazaspiro[4.5]dec-3-en-2-one;

Trans-8-(cyclobutylmethyl)-1-(3-fluorophenyl)-7-methyl-4-[2-(2-methylbenzyl)pyrrolidin-1-yl]-1,3,8-triazaspiro[4.5]dec-3-en-2-one;

trans-4-[2-(3-chlorobenzyl)pyrrolidin-1-yl]-8-(cyclobutylmethyl)-1-(3-fluorophenyl)-7-methyl-1,3,8-triazaspiro[4.5]dec-3-en-2-one;

trans-8-(cyclobutylmethyl)-1-(3-fluorophenyl)-4-[2-(3-methoxybenzyl)pyrrolidin-1-yl]-7-methyl-1,3,8-triazaspiro[4.5]dec-3-en-2-one;

trans-4-[2-(4-chlorobenzyl)pyrrolidin-1-yl]-8-(cyclobutylmethyl)-1-(3-fluorophenyl)-7-methyl-1,3,8-triazaspiro[4.5]dec-3-en-2-one;

trans-8-(cyclobutylmethyl)-4-[2-(2-fluorobenzyl)pyrrolidin-1-yl]-1-(3-fluorophenyl)-7-methyl-1,3,8-triazaspiro[4.5]dec-3-en-2-one;

(5R,7S)-4-[2-(2-chlorobenzyl)pyrrolidin-1-yl]-8-(cyclobutylmethyl)-1-(3-fluorophenyl)-7-methyl-1,3,8-triazaspiro[4.5]dec-3-en-2-one;

5R,7S)-4-(2-benzylpyrrolidin-1-yl)-1-(3-bromophenyl)-8-(cyclobutylmethyl)-7-methyl-1,3,8-triazaspiro[4.5]dec-3-en-2-one; and (5R,7S)-4-(2-benzylpyrrolidin-1-yl)-1-(3-chlorophenyl)-8-(cyclobutylmethyl)-7-methyl-1,3,8-triazaspiro[4.5]dec-3-en-2-one;

or a pharmaceutically acceptable salt thereof.

10. A pharmaceutical composition comprising a therapeutically effective amount of a compound of claim 1, or a pharmaceutically acceptable salt thereof, and a pharmaceutically acceptable carrier.

* * * * *